(12) United States Patent
Xu et al.

(10) Patent No.: US 12,048,755 B2
(45) Date of Patent: Jul. 30, 2024

(54) MICROCAPSULE COMPOSITIONS PREPARED FROM POLYSACCHARIDES

(71) Applicant: International Flavors & Fragrances Inc., New York, NY (US)

(72) Inventors: Li Xu, Edison, NJ (US); Yabin Lei, Holmdel, NJ (US); Ronald Gabbard, Farmingdale, NJ (US); Lewis Michael Popplewell, Morganville, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 17/416,085

(22) PCT Filed: Dec. 17, 2019

(86) PCT No.: PCT/US2019/066844
§ 371 (c)(1),
(2) Date: Jun. 18, 2021

(87) PCT Pub. No.: WO2020/131866
PCT Pub. Date: Jun. 25, 2020

(65) Prior Publication Data
US 2022/0071863 A1  Mar. 10, 2022

Related U.S. Application Data

(60) Provisional application No. 62/899,866, filed on Sep. 13, 2019.

(51) Int. Cl.
| | |
|---|---|
| A61K 8/11 | (2006.01) |
| A61K 8/73 | (2006.01) |
| A61K 8/81 | (2006.01) |
| A61Q 5/02 | (2006.01) |
| A61Q 5/12 | (2006.01) |
| A61Q 15/00 | (2006.01) |
| B01J 13/16 | (2006.01) |
| C11D 3/00 | (2006.01) |
| C11D 3/50 | (2006.01) |

(52) U.S. Cl.
CPC ............... *A61K 8/11* (2013.01); *A61K 8/73* (2013.01); *A61K 8/732* (2013.01); *A61K 8/817* (2013.01); *A61Q 5/02* (2013.01); *A61Q 5/12* (2013.01); *A61Q 15/00* (2013.01); *B01J 13/16* (2013.01); *C11D 3/0015* (2013.01); *C11D 3/505* (2013.01); C11D 2111/12 (2024.01)

(58) Field of Classification Search
CPC . A61K 8/11; A61K 8/73; A61K 8/732; A61K 8/817; A61Q 5/02; A61Q 5/12; A61Q 15/00; B01J 13/16; C11D 3/0015; C11D 3/505; C11D 11/0017
See application file for complete search history.

(56) References Cited

U.S. PATENT DOCUMENTS

| | | | |
|---|---|---|---|
| 3,963,680 | A | 6/1976 | O'Keefe et al. |
| 4,021,595 | A | 5/1977 | Kiritani et al. |
| 5,120,475 | A | 6/1992 | Chen et al. |
| 5,164,126 | A | 11/1992 | Kalishek et al. |
| 5,225,118 | A | 7/1993 | Juang et al. |
| 5,324,584 | A | 6/1994 | Juang et al. |
| 5,705,174 | A | 1/1998 | Benoff et al. |
| 2002/0079599 | A1 | 6/2002 | Kleban et al. |
| 2004/0121155 | A1 | 6/2004 | Matsunami et al. |
| 2005/0153839 | A1 | 7/2005 | Tamura et al. |
| 2005/0161843 | A1 | 7/2005 | Wang et al. |
| 2005/0271735 | A1 | 12/2005 | Stover et al. |
| 2007/0042182 | A1 | 2/2007 | Markus et al. |
| 2007/0138672 | A1* | 6/2007 | Lee ..................... B01J 13/14 264/4.1 |
| 2010/0119679 | A1 | 5/2010 | Dihora et al. |
| 2011/0245141 | A1 | 10/2011 | Gizaw et al. |
| 2012/0148644 | A1 | 6/2012 | Popplewell et al. |
| 2012/0237578 | A1 | 9/2012 | Lei et al. |
| 2013/0330292 | A1 | 12/2013 | Lei et al. |
| 2013/0337023 | A1 | 12/2013 | Lei et al. |
| 2015/0252312 | A1 | 9/2015 | De Villeneuve et al. |
| 2016/0158121 | A1 | 6/2016 | Lei et al. |
| 2016/0193122 | A1* | 7/2016 | Lei ..................... B01J 13/206 424/401 |
| 2017/0191000 | A1* | 7/2017 | Cetti ..................... A61K 8/11 |
| 2017/0252274 | A1 | 9/2017 | Lei et al. |
| 2017/0360676 | A1 | 12/2017 | Dihora et al. |
| 2017/0367373 | A1 | 12/2017 | Bleiel et al. |

(Continued)

FOREIGN PATENT DOCUMENTS

| | | |
|---|---|---|
| EP | 1719554 A2 | 11/2006 |
| EP | 1797946 A2 | 6/2007 |

(Continued)

OTHER PUBLICATIONS

International Preliminary Report on Patentability in PCT/US2019/066844, dated Jun. 16, 2021.
International Search Report and Written Opinion in PCT/US2019/066844, dated Apr. 24, 2020.
Office Communication dated Jun. 22, 2015 from U.S. Appl. No. 13/967,800, filed Aug. 15, 2013.
Office Communication dated Dec. 28, 2015 from U.S. Appl. No. 13/967,800, filed Aug. 15, 2013.

(Continued)

*Primary Examiner* — Doan T Phan

(57) ABSTRACT

Disclosed are microcapsule compositions having microcapsules suspended in an aqueous phase. Each of the microcapsules has a single core-shell structure and contains a microcapsule core and a microcapsule wall encapsulating the microcapsule core. The microcapsule compositions include a pectin. Also disclosed are preparation methods and use of the microcapsule compositions in consumer products.

11 Claims, No Drawings

(56) References Cited

U.S. PATENT DOCUMENTS

| | | | |
|---|---|---|---|
| 2018/0015009 | A1 | 1/2018 | Soubiran et al. |
| 2018/0021241 | A1 | 1/2018 | Lei et al. |
| 2018/0264425 | A1 | 9/2018 | Verstraete et al. |
| 2018/0325786 | A1 | 11/2018 | Lei et al. |
| 2019/0321279 | A1 | 10/2019 | Lei et al. |

FOREIGN PATENT DOCUMENTS

| | | | |
|---|---|---|---|
| EP | 2934464 | B1 | 2/2018 |
| KR | 20030025606 | A | 3/2003 |
| KR | 20160124902 | A | 10/2016 |
| NO | 2016193435 | A1 | 12/2016 |
| WO | 2007137441 | A1 | 12/2007 |
| WO | 2008031241 | A1 | 3/2008 |
| WO | 2011154893 | A1 | 12/2011 |
| WO | 2011161265 | A2 | 12/2011 |
| WO | 2012107323 | A1 | 8/2012 |
| WO | 2013059167 | A2 | 4/2013 |
| WO | 2015023961 | A1 | 2/2015 |
| WO | 2016185171 | A1 | 11/2016 |
| WO | 2017161364 | A1 | 9/2017 |
| WO | 2019063515 | A1 | 4/2019 |
| WO | 2020131855 | A1 | 6/2020 |
| WO | 2020131890 | A1 | 6/2020 |
| WO | 2020131956 | A1 | 6/2020 |
| WO | 2020209907 | A1 | 10/2020 |
| WO | 2020209908 | A1 | 10/2020 |
| WO | 2020209909 | A1 | 10/2020 |

OTHER PUBLICATIONS

Office Communication dated Nov. 18, 2016 from U.S. Appl. No. 13/967,800, filed Aug. 15, 2013.
Office Communication dated Oct. 2, 2017 from U.S. Appl. No. 13/967,800, filed Aug. 15, 2013.
Office Communication dated Aug. 8, 2018 from U.S. Appl. No. 13/967,800, filed Aug. 15, 2013.
Office Communication dated Jan. 7, 2019 from U.S. Appl. No. 13/967,800, filed Aug. 15, 2013.
Office Communication dated Jun. 26, 2019 from U.S. Appl. No. 13/967,800, filed Aug. 15, 2013.
Office Communication dated Dec. 10, 2019 from U.S. Appl. No. 13/967,800, filed Aug. 15, 2013.
Office Communication dated Feb. 26, 2021 in U.S. Appl. No. 16/086,198, filed Sep. 18, 2018.
Office Communication dated Nov. 24, 2020 in U.S. Appl. No. 16/780,158, filed Feb. 3, 2020.
Office Communication dated Jul. 14, 2021 in U.S. Appl. No. 16/780,158, filed Feb. 3, 2020.
Office Communication dated Feb. 17, 2022 in U.S. Appl. No. 16/780,158, filed Feb. 3, 2020.
Office Communication dated May 28, 2020 from U.S. Appl. No. 16/592,033, filed Oct. 3, 2019.
Office Communication dated Nov. 10, 2020 from U.S. Appl. No. 16/592,033, filed Oct. 3, 2019.
Office Communication dated Aug. 5, 2021 from U.S. Appl. No. 16/592,033, filed Oct. 3, 2019.
Office Communication dated Nov. 23, 2021 from U.S. Appl. No. 16/592,033, filed Oct. 3, 2019.

* cited by examiner

MICROCAPSULE COMPOSITIONS PREPARED FROM POLYSACCHARIDES

CROSS-REFERENCE TO RELATED APPLICATIONS

This application is a 371 of International Application No. PCT/US2019/066844 filed Dec. 17, 2019 and claims priority to U.S. Application Ser. No. 62/899,866 filed Sep. 13, 2019. The contents of all applications are incorporated by reference in their entirety.

BACKGROUND

Microcapsules are used in various consumer products where there is a need to deliver, apply, or release an active material including a fragrance, flavor, and malodor counteraction agent to a target area in a time-delayed or controlled manner.

Conventional microcapsules typically have a microcapsule wall formed of a synthetic polymer such as a melamine formaldehyde polymer, a polyurea, or a polyacrylate. Consumers prefer environment friendly, natural materials over synthetic polymers and demand development of green, sustainable products and technologies.

Microcapsules prepared from natural materials have been reported in Mint et al., WO 2016/185171 A1, with a fungal chitosan. Biomolecules have been used to encapsulate fragrance oil. See US 2015/0164117 A1, WO 2016/193435 A1, and US 2018/0078468 A1. Chitosan has also been explored in preparation of microcapsule compositions. See WO 2015/023961 A1, WO 2018/077578 A1, WO 2019/063515 A1, US 2017/0252274 A1, US 2018/0325786 A1, US 2018/0264425 A1, and EP 2 934 464 B1. US 2017/0360676 A1 describes a biodegradable polysaccharide particle that is matrix based but not core-shell microcapsule.

However, these known microcapsules and particles have issues in performance, stability, compatibility, or environmentally degradability. There remains a need to develop environment friendly microcapsules that are high performing, stable, and compatible with consumer products.

SUMMARY OF THE INVENTION

This invention is based on the discovery that certain capsule compositions possess unexpected desirable properties such as high perceived olfactory intensity, great stability, green technology and sustainability.

Accordingly, one aspect of this invention relates to a microcapsule composition containing microcapsules suspended in an aqueous phase. Each of the microcapsules has a single core-shell structure with a particle size of 0.1 μm to 1200 μm in diameter and contains a microcapsule core and a microcapsule wall encapsulating the microcapsule core. The microcapsule core contains an active material (e.g., a fragrance, flavor, cosmetic active, and malodor counteractant) and has a particle size of 0.01 μm to 1000 μm in diameter. The microcapsule composition contains a pectin.

According to one embodiment of this invention, the microcapsule composition further contains a polyphenol component at a level of 0.01% to 5% (e.g., 0.5% to 2.5%, 1% to 2%, and 1.5%) by weight of the microcapsule composition. Preferably, the polyphenol component is derived polyphenol having a molecular weight of 1000 Da to 2,000,000 Da (e.g., 5000 Da to 100,000 Da, and 10000 Da to 500,000 Da).

The microcapsule wall is formed of a polymeric network having a polyisocyanate component at a level of 0.05% to 90% (e.g., 3%-90%) by weight of the polymeric network. Exemplary polyisocyanates include aromatic and aliphatic polyisocyanates. Suitable aromatic polyisocyanates contain a phenyl, tolyl, xylyl, naphthyl, diphenyl moiety, or a combination thereof, such as a polyisocyanurate of toluene diisocyanate, a trimethylol propane-adduct of toluene diisocyanate, and a trimethylol propane-adduct of xylylene diisocyanate. Non-limiting examples of aliphatic polyisocyanates include a trimer of hexamethylene diisocyanate, a trimer of isophorone diisocyanate, a biuret of hexamethylene diisocyanate, and an isocyanurate of hexamethylene diisocyanate.

In any of the microcapsule compositions above, the active material can further contain a pro-fragrance, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or a combination thereof. Preferably, the active material is a high-performing fragrance.

The microcapsule composition can further contain a deposition polymer selected from the group consisting of trimonium, methacrylamidopropyl trimethyl ammonium, acrylamidopropyl trimethylammonium, acrylamide, acrylic acid, dimethyl ammonium, xlylose, galactose, chitosan, hydroxypropylated glucose, hydroxyethylated glucose, hydroxymethylated glucose, vinylamine, ethylenimine, vinylformamide, vinylpyrrollidone, caprolactone, catechol, vinylalcohol, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, a copolymer of acrylamide and 3-methacryloylaminopropyl trimethylammonium, a copolymer of acrylamide and 3-acrylamidopropyl trimethylammonium polymer, a diallyldimethyl-ammoniumchloride polymer and its copolymer, a polysaccharide with saccharide unit functionalized with hydroxypropyl trimmonium, and combinations thereof.

Typically, the microcapsule shell constitutes 10% to 90% by weight of the microcapsule, the microcapsule core constitutes 90% to 10% by weight of the microcapsule, and the microcapsules are present at a level of 10% to 50% by weight of the microcapsule composition. Further, the aqueous phase contains 0.2% to 5% of a dispersant selected from the group consisting of a polyvinyl alcohol, polystyrene sulfonate, carboxymethyl cellulose, naphthalene sulfonate, polyvinylpyrrolidone, copolymer of vinyl pyrrolidone and quaternized dimethylaminoethyl methacrylate, an octenyl succinic anhydride (OSA)-modified starch, OSA-modified gum acacia, gum acacia, alginate, carboxylmethylcellulose, carageenan, xanthan gum, gellan gum, lecithin, modified lecithin, protein, modified protein, pectin, modified pectin, lignin, modified lignin, and combinations thereof.

Another aspect of this invention relates to a microcapsule composition containing microcapsules as described above and one or more polysaccharides selected from the group consisting of pectin, xanthan gum, cornstarch, gum arabic, locust bean gum, maltodextrin, potato starch, modified starch, sodium alginate, xyloglucan, carageenan, gellan gum, and combinations thereof. The polysaccharide preferably has a molecular weight of 200 Da to 2,000,000 Da. The microcapsule shell and core, polyphenol, active material, and deposition polymer are described above.

Also within the scope of this invention is a consumer product containing any of the microcapsule compositions described above. Exemplary consumer products include a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent.

Still within the scope of this invention is a method of preparing a microcapsule composition as described above. The method includes the steps of: (i) providing an oil-in-water emulsion having a plurality of oil droplets dispersed in an aqueous phase, in which the oil-in-water emulsion contains a polyisocyanate, the oil phase contains an active material, and the aqueous phase contains a polysaccharide and optionally a dispersant, and (ii) providing a condition sufficient to induce interfacial polymerization in the oil-in-water emulsion to form a microcapsule slurry that contains microcapsules each having a microcapsule wall encapsulating a microcapsule core, thereby obtaining the microcapsule composition. The interfacial polymerization is typically induced by heating the oil-in-water emulsion to an elevated temperature.

Detailed embodiments of the invention are set forth in the description below. Other features, objects, and advantages of the invention will be apparent from the description and the claims.

DETAILED DESCRIPTION OF THE INVENTION

It has been found that certain polysaccharide microcapsule compositions are environment friendly and compatible with various consumer products with unexpectedly high fragrance performance.

The microcapsule compositions of this invention can be prepared following conventional methods such as those described in US 2018/0325786 A1. In one embodiment, the polysaccharide microcapsules are prepared following the steps of: (i) providing an oil-in-water emulsion having a plurality of oil droplets dispersed in an aqueous phase, in which the oil-in-water emulsion contains a polyisocyanate either in the aqueous or oil phase, the oil phase contains an active material, and the aqueous phase contains a polysaccharide, and optionally a dispersant, and (ii) providing a condition sufficient to induce interfacial polymerization in the oil-in-water emulsion to form a microcapsule slurry that contains microcapsules each having a microcapsule wall encapsulating a microcapsule core, thereby obtaining the microcapsule composition. The interfacial polymerization can be induced by heating the oil-in-water emulsion to an elevated temperature (e.g., at least 25° C., at least 35° C., at least 45° C., at least 55° C., 35° C. to 150° C., and 55° C. to 135° C.).

Optionally, the preparation process further comprises one or both steps of (iii) adding lysine to the microcapsule slurry and (iv) curing the microcapsule slurry at a temperature of 15° C. to 150° C. (e.g., 25° C. to 145° C., 35° C. to 135° C., 45° C. to 135° C., and 55° C. to 135° C.) for 10 minutes to 48 hours (e.g., 15 minutes to 24 hours and 30 minutes to 10 hours).

The oil-in-water emulsion can be prepared using conventional emulsion techniques by emulsifying an oil phase into an aqueous phase with or without a capsule formation aid (i.e., a dispersant). In one embodiment, the oil phase contains the active material (e.g., a hydrophobic active material such as a fragrance), the polyisocyanate and a core solvent (such as caprylic/capric triglyceride). The aqueous phase contains water, polysaccharide, and optionally a surfactant. In another embodiment, the oil phase contains the active material and a core solvent. The aqueous phase contains water, the multi-functional electrophile (e.g., polyisocyanate, glutaraldehyde, and glyoxal), polysaccharide, and optionally a dispersant. In still another embodiment, a polyphenol is added to a pre-formed oil-in-water emulsion, not to either the oil or aqueous phase before the formation of the emulsion. In other embodiments, polysaccharide is added before or after the formation of the emulsion as an aqueous solution or as a solid form. Preferably, a catalyst is added either to the pre-formed emulsion or to the aqueous or oil solution before the formation of the emulsion.

In some embodiments, the process includes a step of adjusting the pH of the oil-in-water emulsion or the microcapsule slurry to 1 to 10 (e.g., 2 to 9, 3 to 8, and 4 to 7). The microcapsule composition thus prepared typically have a pH of 3 to 12 (e.g., 3 to 10, 4 to 9, 5, and 9).

The microcapsule of this invention can also be prepared by printing a microcapsule shell and a microcapsule core using a printing system such as a 3D printer. See WO2016172699A1. Suitable active materials for printing include fragrances, flavors, malodor counteractive agents, cosmetic actives, and nutrients. The printing steps generally include depositing the active materials and the microcapsule shell material in a layer-by-layer fashion, preferably through separate printer heads. The microcapsule shell material can be polymers containing a polysaccharide or of-in-water emulsions as described above.

The microcapsules of this invention each have a core-shell structure with a single microcapsule core and a single microcapsule wall encapsulating the single microcapsule core. The microcapsule wall has an inner surface and outer surface. The inner surface is in contact with the microcapsule core. The outer surface is in contact with the environment where the microcapsule resides, e.g., a water phase, skin, and hair. The microcapsule wall has a thickness (i.e., the distance between the outer surface and the inner surface) of 0.001 µm to 200 µm (e.g., 0.05 µm to 180, 0.01 µm to 150 µm, 0.01 µm to 100 µm, 0.01 µm to 50 µm, 0.01 µm to 20 µm, 0.01 µm to 10 µm, 0.01 µm to 1 µm, and 0.01 µm to 0.5 µm)

The polysaccharide microcapsules of this invention each have a microcapsule wall formed of a polymeric network comprising a polysaccharide component.

A preferred microcapsule composition of this invention has at least three different components: (i) a first component that is a polysaccharide, (ii) a second component derived from a polyisocyanate, and (iii) a third component derived from a polyphenol. Not to be bound by any theory, the first component can be connected to the second component via a covalent bond such as a urethane bond (—NHCOO—); the third component can be connected to the second component via a urethane covalent bond; and the second component polyisocyanate can be self-condensed to form a polyurea polymer. It is believed that an alcohol group (—OH) on the polysaccharide reacts with an isocyanate group (—NCO) on the polyisocyanate to form a urethane bond thus covalently connecting the first component (i.e., the polysaccharide component) with the second component (the polyisocyanate component). Similarly, a hydroxyl group (—OH) on the polyphenol reacts with an isocyanate group on the polyisocyanate to form a polyurethane bond (—OCONH—) therefore covalently connecting the third component (the polyphenol component) to the second component (the polyisocyanate component). It is also possible that a microcapsule of this invention has a multi-layered microcapsule wall, namely, an inner wall formed of a polyurea or polyurethane polymer and an outer wall formed of a polysaccharide. The inner wall is in contact with the microcapsule core and the outer wall. The polyurea polymer of the inner wall can be a self-condensation product of the polyisocyanate. In the emulsion, a polyisocyanate molecule is hydrolyzed on the oil droplet surface to yield a corresponding amine, which in turn reacts with an adjacent polyisocyanate to form a polyurea polymer. The polyurethane polymer of the inner wall can be a reaction product between the polyisocyanate and the polysaccharide (such as pectin and OSA-modified starch), a reaction product between the polyisocyanate and the polyphenol, or a mixture thereof at any ratio (e.g., 1:100 to 100:1, 1:10 to 10:1, and 1:5 to 5:1). The outer polysaccharide wall is in contact with the aqueous phase and is attached to the inner wall, either by non-covalent interactions (e.g., ionic interaction, hydrogen bonding, van der Waals forces, and hydrophobic effect) or by covalent bondings via urethane bonds (—OCONH—), ester bonds (—COO—), ether bonds (—O—), and the like. It is possible that some polysaccharide or the polyphenol is freely suspended in the aqueous phase, without being associated to a microcapsule. Free polysaccharide or polyphenol helps improve the stability and fragrance release profile of the capsule compositions.

Substantivity of these microcapsule walls may be further improved through formulation with cationic, amphoteric and nonionic surfactants and emulsifiers, or by coacervate formation between surfactants and polymers or between different polymers. Combinations of polymeric systems (including those mentioned herein) may be used for this purpose.

Furthermore, polysaccharide or polyphenol components can be chemically (covalently) grafted to the microcapsule wall surface to form into a block, graft or star (with various arms) polymers, which often increase the substantivity toward various surfaces. Alternatively, polysaccharide or polyphenol components associate with the microcapsule wall through physical interactions, such as hydrogen bonding, ionic interactions, hydrophobic interactions, and electron transfer interactions.

The microcapsule wall can comprise from 50% to 100% (e.g., 70% to 100%, 80% to 100%, and 100%) of the polymeric network.

In some embodiments, the microcapsule wall contains 10% to 80% (e.g., 20% to 70%, and 30% to 60%) of the first component (i.e., the polysaccharide component), 10% to 100% (e.g., 5% to 98%, and 10% to 90%) of the second component (i.e., the polyisocyanate component), and 0% to 80% (e.g., 10% to 70% and 20% to 60%) of the third component (i.e., the polyphenol component), by weight of the microcapsule wall, provided that the sum of the first component, the second component, and the third component does not exceed 100%. Optionally, the polymeric network contains one or more additional components such as a polyfunctional amine (such as lysine) or polyfunctional alcohol component at a level of 5% to 80% (e.g., 20% to 70% and 30% to 60%) by weight of the wall.

The microcapsules thus prepared each have a particle size (in diameter) in the range from 0.1 µm to 1000 µm (e.g., 0.5 µm to 500 µm, 1 µm to 200 µm, and 1 µm to 100 µm) with a lower limit of 0.1 µm, 0.5 µm, 1 µm, or 5 µm and an upper limit of 500 µm, 100 µm, 75 µm, 50 µm, or 30 µm.

The microcapsules can be positively or negatively charged with a zeta potential of −200 mV to +200 mV (e.g., 10 mV or greater, 25 mV or greater, 40 mV or greater, 25 mV to 200 mV, and 40 mV to 100 mV) with a lower limit of −200 mV, −150 mV, −100 mV, −50 mV, −25 mV, −10 mV, 0 mV, 10 mV, 20 mV, or 40 mV and an upper limit of 200 mV, 150 mV, 100 mV, 50 mV, 40 mV, 20 mV, 10 mV, 0 mV, −10 mV, and −25 mV. Preferably, the microcapsules each are positively charged. Not to be bound by theory, the positively charged microcapsules have a strong affinity to specific animate and inanimate surfaces (e.g., hair and fabric), and also are unexpectedly stable in certain consumer product bases such as hair conditioners, shampoos, shower gels, and fabric conditioners. The microcapsule compositions of this invention typically contain 10% to 70% (e.g., 15% to 60% and 20% to 50%) of the microcapsules. In one embodiment, the microcapsule compositions comprise a plurality of the microcapsules homogeneously dispersed in an aqueous phase. In another embodiment, the microcapsule compositions comprise the microcapsules in solid form such as spray-dried particles.

The microcapsule compositions are biodegradable. "Biodegradable" as used herein with respect to a material, such as a microcapsule as a whole and/or a biopolymer of the microcapsule shell, has no real or perceived health and/or environmental issues, and is capable of undergoing and/or does undergo physical, chemical, thermal, microbial and/or biological degradation. Ideally, a microcapsule and/or biopolymer is deemed "biodegradable" when the microcapsule and/or biopolymer passes one or more of the Organization for Economic Co-operation and Development (OECD) tests including, but not limited to OECD 301/310 (Ready biodegradation with 60% or more degradation in 28 days or 60 days), OECD 302 (inherent biodegradation with 70% or more biodegradation in 7 days or 14 days), the International Organization for Standardization (ISO) 17556 (solid stimulation studies with 90% or more biodegradation relative to reference in 6 months soil), ISO 14851 (fresh water stimulation studies with 90% or more biodegradation relative to reference in 24 months in water), ISO 18830 (marine sediment stimulation studies with 90% or more biodegradation relative to reference in 24 months in water), OECD 307 (soil stimulation studies with a half life $t_{1/2}$ 180 days or less), OECD 308 (sediment stimulation studies with a half life 180 days or less), and OECD 309 (water stimulation studies with a half life 60 days or less). The composition is deemed biodegradable if it passes other testing methods such as ASTM D5988 and ASTM D5210.

In particular embodiments, the microcapsules are readily biodegradable as determined using the OECD 310 test. The pass level for ready biodegradability under OECD 310 is 60% of $CO_2$ production is reached within the 60-day period of the test.

Polysaccharides

The microcapsule composition of this invention contains one or more species of the polysaccharides, which can be water soluble or non-water soluble. Preferred polysaccharides have a molecular weight of 200 Da to 2,000,000 Da (e.g., 10,000 Da to 500,000 Da and 30,000 Da to 200,000 Da). The water-soluble polysaccharides are, exemplified by polysaccharides of water-soluble natural polymer or water-soluble semi-synthetic polymer. The term "water-soluble" means that about 0.1 g or more of the polysaccharide can be dissolved in 100 ml of water at 25° C.

Non-water soluble polysaccharides include cellulose, methyl cellulose, ethyl cellulose, hydroxypropylmethylcellulose, chitosan, and the like.

Suitable polysaccharides include pectin, xanthan gum, cornstarch, gum arabic, locust bean gum, inulin (blue agava chicory root), maltodextrin, dextrin, cyclodextrin, mannan, potato starch, modified starch, sodium alginate, xyloglucan, carageenan, gellan gum, and combinations thereof.

Pectin is a structural heteropolysaccharide contained in the primary cell walls of terrestrial plants. It is produced commercially (e.g., from Cargill, Minneapolis, MN) as a white to light brown powder, mainly extracted from citrus fruits, berries, apples and other fruit.

The polysaccharide (e.g., pectin) is present at a level of 0.1% to 10% (e.g., 0.1% to 5%, 0.5% to 2.5%, and 1.5%) by weight of the microcapsule composition.

Polyisocyanates

Another class of multi-functional electrophiles are polyisocyanates, each of which has at least two isocyanate (—NCO) groups reactive towards chitosan or multifunctional nucleophiles. The polyisocyanate can be aromatic, aliphatic, linear, branched, or cyclic. It can be water soluble or water dispersible. Alternatively, it is soluble in an organic solvent or fragrance oil. Preferably, the polyisocyanate contains, on average, 2 to 4 isocyanate groups (e.g., at least three isocyanate functional groups). In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

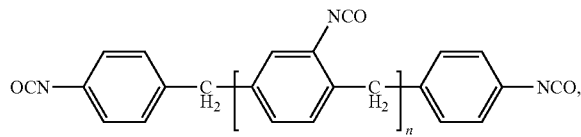

wherein n can vary from zero to a desired number (e.g., 0-50, 0-20, 0-10, and 0-6) depending on the type of crosslinker used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include products under the trade names of LUPRANATE® M20 (chemical name: polymeric methylene diphenyl diisocyanate, i.e., "PMDI"; commercially available from BASF containing isocyanate group "NCO" 31.5 wt %), where the average n is 0.7; PAPI™ 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Covestro, Pittsburgh, Pennsylvania) where the average n is 0.8; MONDUR® MR Light (PMDI containing NCO 31.8 wt %, commercially available from Covestro) where the average n is 0.8; MONDUR® 489 (PMDI commercially available from Covestro containing NCO 30-31.4 wt %) where the average n is 1; poly[(phenylisocyanate)-co-formaldehyde] (Aldrich Chemical, Milwaukee, WI), other isocyanate monomers such as DESMODUR® N3200 (poly(hexamethylene diisocyanate) commercially available from Covestro), and Takenate™ D-110N (trimethylol propane-adduct of xylylene diisocyanate, Mitsui Chemicals America, Inc., Rye Brook, NY, containing NCO 11.5 wt %), DESMODUR® L75 (a polyisocyanate base on toluene diisocyanate commercially available from Covestro), and DESMODUR® IL (another polyisocyanate based on toluene diisocyanate commercially available from Covestro).

The structures of certain polyisocyanates of the invention are shown below:

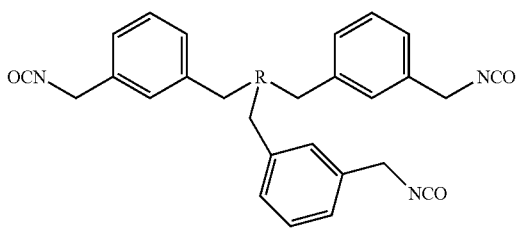

or its structural isomer. R can be a $C_1$-$C_{10}$ alkyl, $C_1$-$C_{10}$ ester, or an isocyanurate. Representative polyisocyanates of this structure are commercially available under the trade names of TAKENATE™ D-110N (Mitsui), DESMODUR® L75 (Covestro), and DESMODUR® IL (Covestro).

Polyisocyanate Takenate™ D-110N and other polyisocyanates are available typically in an ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

As an illustration, Takenate™ D-110N (a trimethylol propane-adduct of xylylene diisocyanate solution in ethyl acetate) is combined with benzyl benzoate and vacuum distilled to remove ethyl acetate to obtain a polyisocyanate solution containing 59% of the trimethylol propane-adduct of xylylene diisocyanate solution and 41% of benzyl benzoate. This polyisocyanate solution has a flash point of at least 60° C. This polyisocyanate solution in benzyl benzoate, together with PVP/PQ-11 or Flexan® II/CMC, can be used to prepare the microcapsule compositions.

Other examples of the aromatic polyisocyanate include 1,5-naphthylene diisocyanate, 4,4'-diphenylmethane diisocyanate (MDI), hydrogenated MDI, xylylene diisocyanate (XDI), tetramethylxylol diisocyanate, 4,4'-diphenyldimethylmethane diisocyanate, di- and tetraalkyl-diphenylmethane diisocyanate, 4,4'-dibenzyl diisocyanate, 1,3-phenylene diisocyanate, 1,4-phenylene diisocyanate, the isomers of toluene diisocyanate (TDI), 4,4'-diisocyanatophenyl-perfluoroethane, phthalic acid bis(isocyanatoethyl) ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include commercial products BAYHYDUR® N302, N303, N304, and N305 series, which are aliphatic water-dispersible based on hexamethylene diisocyanate; DESMODUR® N3600, N3700, and N3900, which are low viscosity, polyfunctional aliphatic polyisocyanates based on hexamethylene diisocyanate; DESMODUR® 3600, N100 and N100A Series, which are aliphatic polyisocyanates based on hexamethylene diisocyanate, available from Covestro, Pittsburgh, PA). More examples include 1-methyl-2,4-diisocyanatocyclohexane, 1,6-diisocyanato-2,2,4-trimethyl-hexane, 1,6-diisocyanato-2,4,4-trimethyl-hexane, 1-isocyanatomethyl-3-isocyanato-1,5,5-tri-methyl-cyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, and dimer fatty acid diisocyanate.

The weight average molecular weight of useful polyisocyanates varies from 200 Da to 5000 Da, 250 Da to 2500 Da, 250 Da to 1000 Da, and preferable from 275 Da to 500 Da.

The range of the polyisocyanate content can vary from 1% to 30% (e.g., 2% to 25%, 3% to 20%, and 5% to 15%) by weight of the microcapsule wall or 0.1% to 5% (e.g., 0.1% to 3.2%, 0.4% to 1%, and 0.6%) by weight of the microcapsule composition.

During the process of preparing the microcapsule composition of this invention, polyisocyanate can be added to the aqueous phase, the oil phase, or the oil-in-water emulsion.

In some embodiments, the polyfunctional isocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the encapsulating polymers as capsule wall materials. More polyisocyanate examples can be found in WO 2004/054362 and WO 2017/192648.

Carbonyl Crosslinkers

Carbonyl crosslinkers can be used together with or to replace polyisocyanate. Carbonyl crosslinkers each have at least two functional groups, e.g., a first and second functional groups.

The first functional group is an electrophilic group reactive towards polysaccharides, polyamines, polyols and other electron-rich groups. Examples include formyl, keto, carboxyl, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an isocyanate group, an α,β-unsaturated carbonyl group, an α,β-unsaturated nitrile group, and an α,β-unsaturated methanesulfonyl group. Preferably, the first function group is a carbonyl electrophilic group containing a carbonyl such as formyl, keto, carboxyl, a carboxylate ester group, an acyl halide group, an amide group, a carboxylic anhydride group, an α,β-unsaturated carbonyl group, a trifluoromethanesulfonate group, and a p-toluenesulfonate group.

The second functional group is an electrophilic group reactive towards polysaccharides, polyamines, polyols and other electro-rich groups. Examples include formyl, keto, carboxyl, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an isocyanate group, an α,β-unsaturated carbonyl group, an α,β-unsaturated nitrile group, an α,β-unsaturated methanesulfonyl group, a trifluoromethanesulfonate group, or a p-toluenesulfonate group. The first functional group and the second functional group can be the same or different.

Examples of a carbonyl crosslinker include glutaric dialdehyde, succinic dialdehyde, and glyoxal; as well as compounds such as glyoxyl trimer and paraformaldehyde, bis(dimethyl) acetal, bis(diethyl) acetal, polymeric dialdehydes, such as oxidized starch. Preferably the cross-linking agent is a low molecular weight, difunctional aldehyde, such as glyoxal, 1,3-propane dialdehyde, 1,4-butane dialdehyde, 1,5-pentane dialdehyde, or 1,6-hexane dialdehyde.

The carbonyl crosslinker can be present at a level of 0.5 to 40% (e.g., 0.5% to 35% and 1% to 30%) by weight of the microcapsule wall.

Multi-Functional Nucleophile

Multi-functional nucleophiles can also be used to form the polymeric network of this invention, in addition to the polysaccharide, polyisocyanate, and polyphenol.

The term "multi-functional nucleophile" refers to an aliphatic or aromatic hydrocarbon onto which is attached two or more nucleophilic groups such as primary/secondary amine groups and the hydroxyl group.

Suitable multi-functional nucleophiles include multi-functional amines (i.e., polyamines) and multi-functional alcohols (i.e., polyols).

In some embodiments, the microcapsule wall of this invention is free of an additional multi-functional amine. In other embodiments, the microcapsule wall contains the polysaccharide and one or more multi-functional amine.

These agents in general contains multiple (i.e., two or more) function groups (e.g., —NH—, —NH$_2$ and —OH) that can react with polyisocyanates to form polyureas or polyurethanes. Examples include multi-functional amines (polyamines) and multi-functional alcohols (polyols). Suitable polyamines contain two or more amine groups including —NH$_2$ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl. Examples include ethylene diamine, 1,3-diaminepropane, diethylene triamine, triethylene tetramine, 1,4-diaminobutane, hexanethylene diamine, hexamethylene diamine, pentaethylenehexamine, diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine. Exemplary polyetheramines include 2,2'-ethylenedioxy)bis (ethylamine) and 4,7,10-trioxa-1,13-tridecanediamine.

Other suitable amines include hexamethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, pentaethylenehexamine, chitosan, nisin, gelatin, 1,3-diaminoguanidine, 1,1-dimethylbiguanide, guanidine, arginine, lysine, ornithine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine, and combinations thereof. See WO 2015/023961 A1 for additional examples.

Amphoteric amines, i.e., amines that can react as an acid as well as a base, are another class of amines of use in this invention. Examples of amphoteric amines include proteins, polypeptides, and amino acids such as a whey protein, a pea protein, a rice protein, a wheat protein, an egg protein, a barley protein, a brown rice protein, a pumpkin seed protein, an oat protein, a potato protein, almond protein, gelatin, legumin, vicilin, convicilin, albumin, globulin or glutelin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include products under the trade names of JEFFAMINE® EDR-148 (where x=2), JEFFAMINE® EDR-176 (where x=3), JEFFAMINE® ED Series, JEFFAMINE® TRIAMINES (from Huntsman), polyethylenimines from BASF (Ludwigshafen, Germany) under the trade names of LUPASOL® (e.g., Lupasol® FG, Lupasol® G20 waterfree, Lupasol® PR 8515, Lupasol® WF, Lupasol® FC, Lupasol® G20, Lupasol® G35, Lupasol® G100, Lupasol® G500, Lupasol® HF, Lupasol® PS, Lupasol® HEO 1, Lupasol® PN50, Lupasol® PN60, Lupasol® PO100 and Lupasol® SK). Other commercially available polyethylenimines include products under the names of EPOMIN® P-1000, EPOMIN® P-1050, EPOMIN® RP18W and EPOMIN® PP-061 from NIPPON SHOKUBAI (New York, NY). Polyvinylamines such as those sold by BASF under the trade name of LUPAMINE® can also be used. A wide range of polyetheramines may be selected by those skilled in the art.

Other suitable polyamines include plant-derived polyamines such as wheat-derived polyamines from a wheat extract, rice-derived polyamines from a rice extract, and a water-soluble powder extracted from rice germ. The latter is extracted from rice germs of *Oryza sativa* Linne with acidic solution (such as a citric acid solution). Plant-derived polyamines generally contain a mixture of various polyamines including spermidine, spermine, putrescine, and the like. Commercially available examples include products under the trade names of *Oryza* Polyamine-P™ and *Oryza* Polyamine-LC™ (BG30), both from *Oryza* oil & Fat Chemical Co., LTD., Ichinomiya, Japan.

Preferred polyfunctional alcohols are polyphenols including those having a 3,4,5-trihydroxyphenyl group or 3,4-dihydropheny group such as tannic acid, which has a typical chemical structure as follows:

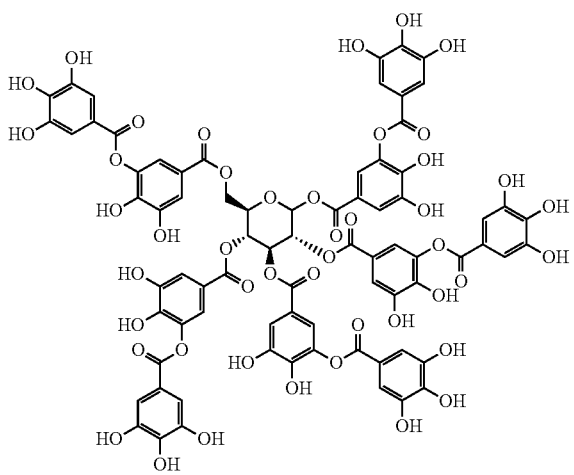

Representative structure of tannic acid

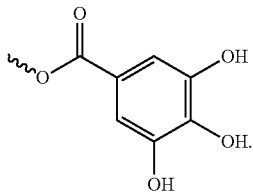

A galloyl moiety

The above chemical formula is often given as $C_{76}H_{52}O_{46}$, which corresponds with decagalloyl glucose. However, commercially available tannic acid typically comprises a mixture of polygalloyl glucoses or polygalloyl quinic acid esters with the number of galloyl moieties per molecule ranging from 2 up to 20 (e.g., 2 to 15 and 2 to 12) and a molecular weight of 400 Daltons to 3500 Daltons (e.g., 496 to 3232 Daltons, 496 Daltons to 2472 Daltons, 180+152n Daltons, and 192+152n Daltons, in which n is between 2 and 13). Tannic acid has a weak acidity (e.g., pKa around 6) with a pH value of 2 to 5 (e.g., 3-4 and 2.5 to 3.5) in an aqueous solution containing 1% of tannic acid. Tannic acid has a water solubility of from 100 g/L to 2850 g/L (e.g., 250 g/L) at 25° C.

Tannic acid is usually extracted from any of the following plant parts: Tara pods (*Caesalpinia spinosa*), gallnuts from *Rhus semialata* or *Quercus infectoria* or Sicilian Sumac leaves (*Rhus coriaria*). Tannic acid is commercially available from suppliers such as Sigma-Aldrich (St Louis) and Ajinomoto OmniChem (Wetteren, Belgium) under the trademarks of Tanal® 01 (polygalloyl glucose, molecular weight 1440 Daltons), Tanal® 02 (polygalloyl glucose, molecular weight 1040 Daltons), and Tanal® 04 (polygalloyl quinic acid ester, molecular weight 860 Daltons).

In additional to polyphenols, other polyols can also be used. See polyols described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, polyphenol, and combinations thereof.

Multi-functional aldehydes such as glutaraldehyde and glyoxal form derivatives such as monohydrates, dehydrates, acetal, or hemiacetal in aqueous solution under certain pH ranges (i.e., in an acidic condition). These multi-functional aldehyde derivatives have hydroxyl (—OH) groups that are reactive toward polyisocyanates to form polyurethane bonds. As such, multi-functional aldehydes act as multi-functional nucleophiles under certain conditions such as at a pH of 3 to 8.

The multi-functional nucleophile can be present at a level of 0 to 40% (e.g., 1% to 35%, 5% to 35%, and 10% to 30%) by weight of the microcapsule wall or 0 to 10% (e.g., 0.01% to 8%, 0.02% to 7%, 0.1% to 5%, and 0.2% to 3%) by weight of the microcapsule composition.

Capsule Formation Aids

The microcapsule composition is typically prepared in the presence of a capsule formation aid, which can be a surfactant or dispersant. Capsule formation aids also improve the performance of the microcapsule composition. Performance is measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener or detergent. The post-rub phase is after the capsules have been deposited and broken by friction or other mechanisms.

The capsule formation aid can be a protective colloid or emulsifier, e.g., maleic-vinyl copolymers such as vinyl ethers with maleic anhydride or acid copolymers, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose, fatty acid esters of polyoxy-ethylenated sorbitol, sodium dodecylsulfate, nonionic surfactants (such as alkoxylated alcohols, alkoxylated castor oils, and alkoxylated fatty acids), and combinations thereof. The concentration of the capsule formation aid (e.g., the surfactant and dispersant) varies from 0.1% to 5% (e.g., 0.2% to 4%, 0.5% to 4%, 0.5% to 2.5%, and 1% to 2%) by weight of the capsule composition.

Commercially available surfactants include, but are not limited to, sulfonated naphthalene-formaldehyde condensates such as MORWET® D-425 (sodium salt of alkylnaphthalenesulfonate formaldehyde condensate, commercially available from Akzo Nobel, Fort Worth, Texas); polyoxyethylated castor oil (a nonionic surfactant commercially available under the trademark of Toximul® 8240 from Stepan, Chicago, Illinois); partially hydrolyzed polyvinyl alcohols under the trade names of MOWIOL®, e.g., MOWIOL® 3-83 (commercially available from Kuraray, Houston, Texas); ethylene oxide-propylene oxide block copolymers or poloxamers such as PLURONIC®, SYNPERONIC® or PLURACARE® (BASF); sulfonated polystyrenes such as FLEXAN® II (Akzo Nobel); ethylene-maleic anhydride polymers such as ZEMAC® (Vertellus Specialties Inc., Indianapolis, Indiana); and Polyquaternium series such as Polyquaternium 11 ("PQ11;" a copolymer of vinyl pyrrolidone and quaternized dimethylaminoethyl methacrylate; sold by BASF as LUVIQUAT® PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with carboxymethyl cellulose (CMC), polyvinylpyrrolidone, polyvinyl alcohol, alkylnaphthalenesulfonate formaldehyde condensates, and/or a surfactant during processing to facilitate capsule formation. Examples of these surfactants include cetyl trimethyl ammonium chloride (CTAC), poloxamers under the trade name of PLURONIC® (e.g., F127), PLURAFAC® (e.g., PLURAFAC® F127), or MIRANET-N®, saponins such as QNATURALE® (National Starch Food Innovation); or a gum Arabic such as Seyal or Senegal. In certain embodiments, the CMC polymer has a molecular weight (e.g., weight average molecular weight) range between 90,000 Da and 1,500,000 Da, preferably between 250,000 Da and 750,000 Da and more preferably between 400,000 Da and 750,000 Da. The CMC polymer has a degree of substitution between 0.1 and 3, preferably between 0.65 and 1.4, and more preferably between 0.8 and 1. The CMC polymer is present in the capsule slurry at a level from 0.1% to 2% and preferably from 0.3% to 0.7%. In other embodiments, polyvinylpyrrolidone used in this invention is a water-soluble polymer and has a molecular weight (e.g., weight average molecular weight) of 1,000 Daltons to 10,000,000 Daltons. Suitable polyvinylpyrrolidones include K12, K15, K17, K25, K30, K60, K90, and mixtures thereof. The polyvinylpyrrolidone can present at 2% to 50%, 5% to 30%, or 10% to 25% by weight of the microcapsule composition.

Catalysts

In sometime embodiments, a catalyst is added to induce the interfacial polymerization in the formation of a capsule wall. Examples include metal carbonates, metal hydroxide, amino or organometallic compounds and include, for example, sodium carbonate, cesium carbonate, potassium carbonate, lithium hydroxide, ammonium persulfate, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate, and dibutyltin dilaurate.

Other Encapsulating Polymers

The microcapsule composition of this invention optionally has a second, third, fourth, fifth, or sixth microcapsule each formed of an encapsulating polymer selected from the group consisting of a sol-gel polymer (e.g., silica), polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof. A branched polyethyleneimine and its derivatives can also be coated onto the microcapsule wall to prepare a microcapsule having a positive zeta potential.

These encapsulating polymers are described in detail below.

Sol-gel Microcapsules. These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

Preferred examples are the silicic acid esters such as tetramethyl orthosilicate (TMOS) and tetraethyl orthosilicate (TEOS) such as product under the trademark of Dynasylan® (organofunctional silanes commercially available from Degussa Corporation, Parsippany New Jersey, USA). Other sol-gel precursors include various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Polyacrylate microcapsules, polyacrylamide microcapsules, and poly(acrylate-co-acrylamide) microcapsules. These microcapsules are prepared from corresponding precursors, which form the microcapsule wall. Preferred precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/ acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethyloipropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is typically polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1,1'-azobis-(cyclohexane-1-carbonitrile), dimethyl 2,2'-azobis(2-methylpropionate), 2,2'-azobis[2-methyl-N-(2-hydroxyethyl) propionamide, sodium persulfate, benzoyl peroxide, and combinations thereof.

Emulsifiers used in the formation of these capsule walls are typically anionic emulsifiers including without limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfo-succinates, dioctyl sulfosuccinate, sodium dilaurylsulfosuccinate, poly (styrene sulfonate) sodium salt, isobutylene-maleic anhydride copolymer, gum arabic, sodium alginate, carboxymethyl cellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropane-sulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1% to 40% by weight of all constituents, more preferably from 0.5% to 10%, more preferably 0.5% to 5% by weight.

Aminoplasts and Gelatin. A representative process used for aminoplast encapsulation is disclosed in U.S. Pat. No. 3,516,941 and US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB 2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine formaldehyde Capsules. Urea-formaldehyde and melamine-formaldehyde precondensate capsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing this invention, the resulting material has a weight average molecular weight in the range of from 156 Da to 3000 Da. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 6,261,483, and Lee et al. (2002) *J. Microencapsulation* 19, 559-569.

Examples of urea-formaldehyde pre-condensates useful in the practice of this invention are URAC™ 180 and URAC™ 186, trademarks of Cytec Technology Corp. of Wilmington, DE. Examples of melamine-formaldehyde pre-condensates useful in the practice if this invention, include, but are not limited to, CYMEL® U-60, CYMEL® U-64 and CYMEL® U-65, trademarks of Cytec Technology Corp. of Wilmington, DE. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from 9:1 to 1:9, preferably from 5:1 to 1:5 and most preferably from 2:1 to 1:2.

In one embodiment, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN® series of polyvinyl formamides available from BASF. The weight average molecular weights of these materials can range from 10,000 Da to 1,000,000 Da.

These capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are used in products having low pH, e.g., fabric conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

The microcapsule composition of this invention optionally contains one or more additional microcapsules, e.g., a second, third, fourth, fifth, or sixth microcapsules. Each of these microcapsules can be any of the microcapsule described above.

These additional microcapsules can be any microcapsules described above but different from each other in term of microcapsule size, degree of polymerization, degree of crosslinking, encapsulating polymer, thickness of the wall, active material, ratio between the wall material and the active material, rupture force or fracture strength, and the like.

Active Materials

The microcapsule core can include one or more active materials such as flavors and/or fragrance ingredients (e.g., fragrance oils). Exemplary active materials include those listed on page 38-50 of WO 2016049456. These active material include flavor or fragrance ingredients, taste masking agents, taste sensates, malodor counteracting agents, vitamins or derivatives thereof, antibacterials, sunscreen actives, antioxidants, anti-inflammatory agents, fungicide, anesthetics, analgesics, antifungal agents, antibiotics, anti-viral agents, anti-parasitic agents, anti-infectious, anti-acne agents, dermatological active ingredients, enzymes and co-enzymes, skin whitening agents, anti-histamines, chemotherapeutic agents, insect repellents, emollient, skin moisturizing agent, wrinkle control agent, UV protection agent, fabric softener active, hard surface cleaning active, skin or hair conditioning agent, animal repellent, vermin repellent, flame retardant, antistatic agent, nanometer to micron size inorganic solid, polymeric or elastomeric particle, and combination thereof.

High performing, high impact fragrances are envisaged. One class of high performing fragrances is described in WO 2018/071897. These fragrances have a high intensity accord containing (i) at least 7 wt % (e.g., 7 to 95 wt %) of Class 1 fragrance ingredients, (ii) 5 to 95 wt % (e.g., 5 to 80 wt %, 10 to 80 wt %, and 10 to 70 wt %) of Class 2 fragrance ingredients, and (iii) 0 to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less. In some embodiments, the sum of the Class 1 fragrance ingredients, the Class 2 fragrance ingredients, and the Class 3 fragrance ingredients is 100%. In other embodiments, the sum of Class 1 and Class 2 ingredients is 20% to 100 wt %. Other high impact fragrances suitable for use in this invention are those described in WO 1999/065458, U.S. Pat. No. 9,222,055, US 2005/0003975, and WO1997/034987.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xanthophylls (flavoxanthin, lutein, cryptoxanthin, rubixanthin, violaxanthin, rodoxanthin), fast carmine (carminic acid, cochineal), azorubin, cochineal red A (Ponceau™ 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a ClogP of 0.5 to 15 are employed. For instance, the ingredients having a ClogP value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

It is preferred that a fragrance having a weight-averaged ClogP of 2.5 and greater (e.g., 3 or greater, 2.5 to 7, and 2.5 to 5) is employed. The weight-averaged ClogP is calculated as follows:

$$ClogP = \{Sum[(Wi)(ClogP)i]\}/\{SumWi\},$$

in which Wi is the weight fraction of each fragrance ingredient and (ClogP)i is the ClogP of that fragrance ingredient.

As an illustration, it is preferred that greater than 60 wt % (preferably greater than 80 wt % and more preferably greater than 90 wt %) of the fragrance chemicals have ClogP values of greater than 2 (preferably greater than 3.3, more preferably greater than 4, and even more preferably greater than 4.5).

Those with skill in the art will appreciate that many fragrances can be created employing various solvents and fragrance chemicals. The use of a relatively low to intermediate ClogP fragrance ingredients will result in fragrances suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high ClogP materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5% to 95% (e.g., 10% to 90%, 15% to 90%, and 20% to 80%) by weight of the microcapsule composition. The amount of the capsule wall is from 0.5% to 30% (e.g., 1% to 25%, 2 to 20% and 5 to 15%) also by weight of the microcapsule composition. In other embodiments, the amount of the encapsulated active material is from 15% to 99.5% (e.g., 20% to 98% and 30% to 90%) by weight of the microcapsule, and the amount of the capsule wall is from 0.5% to 85% (e.g., 2 to 50% and 5 to 40%) by weight of the microcapsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of 0.01% to 40% (e.g., 0.5% to 30%) by weight of the microcapsule.

Suitable examples include those described in WO 2016/049456, pages 55-57 and US 2016/0158121, pages 15-18.

Deposition Aids

An exemplary deposition aid useful in the microcapsule composition of this invention is a copolymer of acrylamide and acrylamidopropyltrimonium chloride. This copolymer facilitates the deposition of the microcapsule onto a hard surface (e.g., hair, skin, fiber, furniture, and floor). The copolymer generally has an average molecular weight (e.g., weight average molecular mass (Mw) determined by size exclusion chromatography) of 2,000 Da to 10,000,000 Da with a lower limit of 2,000 Da, 5,000 Da, 10,000 Da, 20,000 Da, 50,000 Da, 100,000 Da, 250,000 Da, 500,000 Da, or 800,000 Da and an upper limit of 10,000,000 Da, 5,000,000 Da, 2,000,000 Da, 1,000,000 Da, or 500,000 Da (e.g., 500,000 Da to 2,000,000 Da and 800,000 Da to 1,500,000 Da). The charge density of the copolymer ranges from 1 meq/g to 2.5 meq/g, preferably from 1.5 meq/g to 2.2 meq/g. The copolymer of acrylamide and acrylamide-propyltrimonium chloride is commercially available from various vendors such as Ashland as N-Hance® SP-100 and Ciba SAL-CARE® SC60.

Other suitable deposition aids include anionically, cationically, nonionically, or amphoteric water-soluble polymers. Suitable deposition aids trimonium, methacrylamidopropyl trimethyl ammonium, acrylamidopropyl trimethylammonium, acrylamide, acrylic acid, dimethyl ammonium, xlylose, galactose, hydroxypropylated glucose, hydroxyethylated glucose, chitosan, hydroxymethylated glucose, vinylamine, ethylenimine, functionalized branched polyethylenimine, vinylformamide, vinylpyrollidone, caprolactone, catechol, vinylalcohol, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79 and hydrolyzed keratin co-polymer, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, a copolymer of acrylamide and methacrylamidopropyltrimonium chloride, a copolymer of acrylamide and acrylamidopropyltrimonium chloride, a 3-acrylamidopropyl trimethylammonium polymer or its copolymer, a 3-methacrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkyl-monium hydroxypropyl hydrolyzed protein, and combinations thereof. More examples of the deposition aids are described in WO 2016049456, pages 13-27; US 2013/0330292; US 2013/0337023; and US 2014/0017278.

Additional depositional aids are those cationic polymers described in WO2016032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g. The cationic polymers are comprised of structural units that are nonionic, cationic, anionic, or mixtures thereof. In some aspects, the cationic polymer comprises from 5 mol % to 60 mol %, or from 15 mol % to 30 mol %, of a nonionic structural unit derived from a monomer selected from the group consisting of (meth)acrylamide, vinyl formamide, N,N-dialkyl acrylamide, N,N-dialkyl-methacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer comprises a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkyll-trialkylamminium salts, vinylamine, vinylimine, vinyl imidazole, quaternized vinyl imidazole, diallyl dialkyl ammonium salts, and mixtures thereof. Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methyl-ammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer comprises an anionic structural unit at a level of 0.01 mol % to 15 mol %, 0.05 mol % to 10 mol %, or 0.1 mol % to 5 mol % by mass of the cationic polymer. In some aspects, the anionic structural unit is derived from an anionic monomer selected from the group consisting of acrylic acid, methacrylic acid, maleic acid, vinyl sulfonic acid, styrene sulfonic acid, acrylamidopropylmethane sulfonic acid (AMPS) and their salts, and mixtures thereof.

Exemplary cationic polymers are polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% can be added to the microcapsule composition. The second capsule formation deposition aid can be selected from the above-described deposition aid.

Additional Components

The microcapsule composition of this invention can include one or more non-confined or unencapsulated active materials from 0.01 to 50%, more preferably from 5 to 40%.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Examples of additional components include those described in US 2016/0158121.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate.

Likewise, a salt can also be formed between a cation and a negatively charged group on the compound, polymer, or agent. Suitable cations include sodium ion, potassium ion, magnesium ion, calcium ion, and an ammonium cation (e.g., tetramethyl-ammonium ion). A precursor can be ester and another suitable derivative, which, during the process of preparing a capsule composition of this invention, is capable of converting to the compound, polymer, or agent and being used in preparing the capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

The microcapsule composition of this invention can be a slurry containing in a solvent (e.g., water) the capsule at a level 0.1% to 80% (preferably 1% to 65% and more preferably 5% to 45%) by weight of the capsule delivery system. An exemplary microcapsule composition of this invention contains a plurality of microcapsules each dispersed in an aqueous phase and is stable for at least 7 days (e.g., at least 10 days, at least 30 days, and at least 60 days) at 40° C.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of 21 $s^{-1}$ and a temperature of 25° C. In certain embodiments, the viscosity of a microcapsule composition of this invention is less than 3000 cP at a shear rate of 21 $s^{-1}$ and a temperature of 25° C.

Stability of a microcapsule can be assessed using a number of different approaches including physical stability and/or storage stability. When assessing physical stability, an exemplary microcapsule composition may be dispersed in an aqueous phase and shown to be stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

When assessing storage stability, fragrance retention within the microcapsule may be measured directly after storage at a desired temperature and time periods such as four weeks, six weeks, two months, three months or more in a consumer product base. The preferred manner is to measure total headspace of the consumer product at the specified time and to compare the results to the headspace of a control consumer product made to represent 0% retention via direct addition of the total amount of fragrance present. Alternatively, the consumer product may be performance tested after the storage period and the performance compared to the fresh product, either analytically or by sensory evaluation. This measurement often involves either measuring the fragrance headspace over a substrate used with the product, or odor evaluation of the same substrate. In certain embodiments, retention of the active material in the core of the instant microcapsules is assessed in a consumer product base, e.g., under storage conditions such as at a temperature in the range of 25° C. to 40° C., or more preferably in the range of 30° C. to 37° C., or most preferably 37° C., for an extended period of time of at least 2 weeks, 4 weeks, 6 weeks, 8 weeks, 16 weeks, or 32 weeks. In certain embodiments, the microcapsules of this invention retain at least 40%, 45%, 50%, 55%, 60%, 65%, 70%, 75%, 80%, 85%, 90%, 95%, or 99% of the active material when added to a consumer product base. In particular embodiments, the microcapsules of this invention, when added to a consumer product base, retain between 40% and 90% of the active material after being stored at 37° C. for at least 4 weeks, 8 weeks or 12 weeks. Alternatively stated, the microcapsules of this invention lose less than 50% of the active material due to leakage when added to a consumer product base and stored for 8 weeks at 37° C.

Using a process of this invention, a relatively high encapsulation efficiency is achieved. "Encapsulation efficiency" or "microencapsulation efficiency" or "MEE" represents the proportion of the active material core that is not available to an extracting solvent under specified test conditions. In accordance with the method of this invention, microencapsulation efficiencies in the range of 50% to 99.9% are attainable, or more preferably 60% to 99.7%. In particular, encapsulation efficiencies of at least 90%, 92%, 94%, 96%, 98%, or 99% are achieved.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also dried, e.g., spray dried, heat dried, and belt dried, to a solid form. In a spray drying process, a spray dry carrier is added to a microcapsule composition to assist the removal of water from the slurry. See US20120151790, US20140377446, US20150267964, US20150284189, and US20160097591.

According to one embodiment, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1% to 50%, more preferably from 5% to 20%, by weight of the microcapsule composition in slurry.

Optionally, a free flow agent (anticaking agent) of silicas which may be hydrophobic (i.e. silanol surface treated with halogen silanes, alkoxysilanes, silazanes, siloxanes, etc. such as Sipernat® D17, Aerosil® R972 and R974 (available from Degussa), etc.) and/or hydrophilic such as Aerosil® 200, Sipernat® 22S, Sipernat® 50S, (available from Degussa), Syloid® 244 (available from Grace Davison), may be present from 0.01% to 10%, more preferable from 0.5% to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature is in the range of 150° C. to 240° C., preferably between 170 and 230° C., more preferably between 190° C. and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid capsule slurry is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The microcapsule of this invention can be positively or negatively charged with a zeta potential in the range of −200 mV to +200 mV, e.g., at least 10 mV, at least 25 mV, at least 40 mV, 25 mV to 200 mV, and 40 mV to 100 mV.

Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule.

The zeta potential is an important indicator of the stability of the microcapsule in compositions or consumer products. Typically, a microcapsule having a zeta potential of 10 mV to 25 mV shows a moderate stability. Similarly, a microcapsule having a zeta potential of 25 mV to 40 mV shows a good stability and a microcapsule having a zeta potential of 40 mV to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin and Goetz, "Ultrasound for characterizing colloids", Elsevier, 2002.

The microcapsule of this invention has a fracture strength of 0.2 MPa to 80 MPa (e.g., 0.5 MPa to 60 MPa, 1 MPa to 50 MPa, and 5 MPa to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang et al., *J. Microencapsulation* 18(5), 593-602 (2001).

The microcapsule of this invention has a rupture force of less than 10 millinewtons ("mN") such as 0.1 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang et al., *Journal of Microencapsulation* 16(1), 117-124 (1999).

Applications

The microcapsule composition of this invention can be added to a consumer product base directly or be printed onto a product base or a movable product conveyor (e.g., a non-stick belt) for drying. See International Application Publication WO2019212896A1. In a typical printing system, the microcapsule composition is printed onto a movable product conveyor that directly receives the printed microcapsule, which is then dried on the movable product conveyor to produce a dried product. Additional carriers and solvent can be added to the microcapsule composition before printing. In some embodiments, the viscosity of the microcapsule composition is adjusted to more than 500 cP or more than 1000 cP with a viscosity modifier. With reference to the print assembly, the print assembly can include a print head or array of nozzles and optionally be adapted to print the microcapsule in a dot pattern (e.g., arranged to facilitate drying, post-processing, and product quality). Optional features of the system include, a dehumidifier configured to supply desiccated air to the drying component; a supplemental energy source (e.g. a radiant heat source), for facilitating drying of the printed microcapsule; and/or a product discharge component for removing dried product from the movable product conveyor.

The microcapsule of the present invention is well-suited for use, without limitation, in the following additional products:

a) Household products
   i. Liquid or Powder Laundry Detergents which can use the present invention include those systems described in U.S. Pat. Nos. 5,929,022, 5,916,862, 5,731,278, 5,565,145, 5,470,507, 5,466,802, 5,460, 752, 5,458,810, 5,458,809, 5,288,431, 5,194,639, 4,968,451, 4,597,898, 4,561,998, 4,550,862, 4,537, 707, 4,537,706, 4,515,705, 4,446,042, and 4,318,818
   ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
   iii. Scent Boosters such as those described in U.S. Pat. Nos. 7,867,968, 7,871,976, 8,333,289, US 2007/0269651 A1, and US2014/0107010 A1.
   iv. Fabric Care Products such as Rinse Conditioners (containing 1-30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574, 179, 5,562,849, 5,545,350, 5,545,340, 5,411,671, 5,403,499, 5,288,417, and 4,767,547
      Liquid fabric softeners/fresheners contain at least one fabric softening agent present, preferably at a concentration of 1-30% (e.g., 4-20%, 4-10%, and 8-15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01-2.5%, preferably 0.02-1.25% and more preferably 0.1-0.63%. As another example, when the fabric softening agent is 20% by weight of the fabric softener, the active material is 0.04-10%, preferably 0.08-5% and more preferably 0.4-2.5%. The active material is a fragrance, malodor counteractant or mixture thereof. The liquid fabric softener can have 0.15-15% of capsules (e.g., 0.5-10%, 0.7-5%, and 1-3%). When including capsules at these levels, the neat oil equivalent (NOE) in the softener is 0.05-5% (e.g., 0.15-3.2%, 0.25-2%, and 0.3-1%).
      Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.
  v. Liquid dish detergents such as those described in U.S. Pat. Nos. 6,069,122 and 5,990,065
  vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
  vii. All-purpose Cleaners including bucket dilutable cleaners and toilet cleaners
  viii. Bathroom Cleaners
  ix. Bath Tissue
  x. Rug Deodorizers
  xi. Candles
  xii. Room Deodorizers
  xiii. Floor Cleaners
  xiv. Disinfectants
  xv. Window Cleaners
  xvi. Garbage bags/trash can liners
  xvii. Air Fresheners including room deodorizer and car deodorizer, scented candles, sprays, scented oil air freshener, Automatic spray air freshener, and neutralizing gel beads
  xviii. Moisture absorber
  xix. Household Devices such as paper towels and disposable Wipes
  xx. Moth balls/traps/cakes
  xxi. Liquid fragrance compositions each comprising: (i) 3 wt % to 40 wt % (e.g., 5 wt % to 35 wt %, preferably 8 wt % to 30 wt %, and more preferably 10 wt % to 3 wt %) of a fragrance in the form of neat oil or encapsulated in a microcapsule, (ii) 0.5 wt % to 5 wt % (preferably 0.2 wt % to 3 wt %, and more preferably 0.5 wt % to 2.5 wt %) of glyceryl ricinoleate, and (iii) 60 wt % to 95 wt % of water. All amounts are based on the weight of the liquid fragrance composition.
b) Baby Care Products
  i. Diaper Rash Cream/Balm
  ii. Baby Powder
c) Baby Care Devices
  i. Diapers
  ii. Bibs
  iii. Wipes
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
  i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6. flavor oil 1-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.
  ii. Tooth Powder
  iii. Oral Rinse
  iv. Tooth Whiteners
  v. Denture Adhesive
e) Health Care Devices
  i. Dental Floss
  ii. Toothbrushes
  iii. Respirators
  iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant x. Wax-based Deodorant. An exemplary formulation as follows:
  1. Parafin Wax 10-20%
  2. Hydrocarbon Wax 5-10%
  3. White Petrolatum 10-15%
  4. Acetylated Lanolin Alcohol 2-4%
  5. Diisopropyl Adipate 4-8%
  6. Mineral Oil 40-60%
  7. Preservative (as needed)
    The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.

xi. Glycol/Soap Type Deodorant. An exemplary formulation as follows:
  1. Propylene Glycol 60-70%
  2. Sodium Stearate 5-10%
  3. Distilled Water 20-30%
  4. 2,4,4-Trichloro-2'-Hydroxy Diphenyl Ether, manufactured by the Ciba-Geigy Chemical Company and a Trademark of the Ciba-Geigy Chemical Company) 0.01-0.5%
    The ingredients are combined and heated to 75° C. with stirring until the sodium stearate has dissolved. The resulting mixture is cooled to 40° C. followed by addition of a composition of this invention.

xii. Lotion including body lotion, facial lotion, and hand lotion
xiii. Body powder and foot powder
xiv. Toiletries
xv. Body Spray
xvi. Shave cream and male grooming products
xvii. Bath Soak
xviii. Exfoliating Scrub h) Personal Care Devices
  i. Facial Tissues
  ii. Cleansing wipes i) Hair Care Products
  i. Shampoos (liquid and dry powder)
  ii. Hair Conditioners (Rinse-out conditioners, leave-in conditioners, and cleansing conditioners)
  iii. Hair Rinses
  iv. Hair Refreshers
  v. Hair perfumes
  vi. Hair straightening products
  vii. Hair styling products, Hair Fixative and styling aids
  viii. Hair combing creams
  ix. Hair wax
  x. Hair foam, hair gel, nonaerosol pump spray
  xi. Hair Bleaches, Dyes and Colorants
  xii. Perming agents
  xiii. Hair wipes j) Beauty Care
  i. Fine Fragrance—Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%)
    2. Water (0-99%)
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1%)
    4. Optionally an emulsifier or an emollient may be included including but not limited to those listed above
  ii. Solid Perfume
  iii. Lipstick/lip balm
  iv. Make-up cleanser
  v. Skin care cosmetic such as foundation, pack, sunscreen, skin lotion, milky lotion, skin cream, emollients, skin whitening
  vi. Make-up cosmetic including manicure, mascara, eyeliner, eye shadow, liquid foundation, powder foundation, lipstick and cheek rouge k) Consumer goods packaging such as fragranced cartons, fragranced plastic bottles/boxes l) Pet care products
  i. Cat litter
  ii. Flea and tick treatment products
  iii. Pet grooming products
  iv. Pet shampoos
  v. Pet toys, treats, and chewables
  vi. Pet training pads
  vii. Pet carriers and crates m) Confectionaries confectionery, preferably selected from the group consisting of chocolate, chocolate bar products, other products in bar form, fruit gums, hard and soft caramels and chewing gum
  i. Gum
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709) 20-25%
    2. Powdered sugar 45-50%
    3. glucose 15-17%
    4. starch syrup 10-13%
    5. plasticizer 0.1%
    6. flavor 0.8-1.2%
      The components described above were kneaded by a kneader according to the foregoing formulation to provide a chewing gum. Encapsulated Flavor or sensate is then added and blended till homogeneous.
  ii. Breath Fresheners
  iii. Orally Dissolvable Strips
  iv. Chewable Candy
  v. Hard Candy n) Baked products, preferably selected from the group consisting of bread, dry biscuits, cakes and other cookies;
o) snack foods, preferably selected from the group consisting of baked or fried potato chips or potato dough products, bread dough products and corn or peanut-based extrudates;
 i. Potato, tortilla, vegetable or multigrain chips
 ii. Popcorn
 iii. Pretzels
 iv. Extruded stacks
p) Cereal Products preferably selected from the group consisting of breakfast cereals, muesli bars and pre-cooked finished rice products
q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
 i. Ready to drink liquid drinks
 ii. Liquid Drink Concentrates
 iii. Powder Drinks
 iv. Coffee: Instant Cappucino
  1. Sugar 30-40%
  2. Milk Powder 24-35%
  3. Soluble Coffee 20-25%
  4. Lactose 1-15%
  5. Food Grade Emulsifier 1-3%
  6. Encapsulated Volatile Flavor 0.01-0.5%
 v. Tea
 vi. Alcoholic
r) Spice blends and consumer prepared foods
 i. Powder gravy, sauce mixes
 ii. Condiments
 iii. Fermented Products
s) Ready to heat foods: ready meals and soups, preferably selected from the group consisting of powdered soups, instant soups, precooked soups
 i. Soups
 ii. Sauces
 iii. Stews
 iv. Frozen entrees
t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
 i. Yoghurt
 ii. Ice cream
 iii. Bean Curd
 iv. Cheese
u) Soya protein or other soybean fractions, preferably selected from the group consisting of soya milk and products produced therefrom, soya lecithin-containing preparations, fermented products such as tofu or tempeh or products produced therefrom and soy sauces;
v) Meat products, preferably selected from the group consisting of ham, fresh or raw sausage preparations, and seasoned or marinated fresh or salt meat products
w) Eggs or egg products, preferably selected from the group consisting of dried egg, egg white and egg yolk
x) Oil-based products or emulsions thereof, preferably selected from the group consisting of mayonnaise, remoulade, dressings and seasoning preparations
y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables
z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

Consumer Product Base

The microcapsules of this invention are suitable to incorporate into a consume product base either as a slurry or in a dry form. As used herein, a "consumer product base" refers to a composition for use as a consumer product to fulfill specific actions, such as cleaning, softening, and caring or the like. Components of the consumer product base may include any suitable additive that produces an intended effect under intended use conditions of the consumer product. For example, consumer product base ingredients may be selected from the group of personal cleansing and/or conditioning agents such as hair care agents including shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof. Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of compounds may be useful for one or more of the agents listed above. For example, surfactants may be used for any number of the agents described above. Likewise, bleaching agents may be used for fabric care, hard surface cleaning, dishwashing and even teeth whitening. Therefore, one of ordinary skill in the art will appreciate that the agents will be selected based upon the desired intended use of the consumer product. For example, if a consumer product is for hair care and/or conditioning then one or more suitable surfactants, such as a lathering surfactant could be selected to provide the desired benefit to a consumer. Similarly, if a consumer product is for laundering clothes in a laundry operation, then one or more suitable surfactants and/or enzymes and/or builders and/or perfumes and/or suds suppressors and/or bleaching agents could be selected to provide the desired benefit to a consumer.

In one example, the agent is a non-perfume ingredient. In another example, the agent is a non-surfactant ingredient. In still another example, the agent is a non-ingestible ingredient, in other words an agent other than an ingestible ingredient.

In certain embodiments, the consumer product base includes one or more bleach activators, surfactants, builders, chelating agents, dye transfer inhibiting agents, dispersants, enzymes, and enzyme stabilizers, catalytic metal complexes, polymeric dispersing agents, deposition agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments, and combinations thereof. The precise nature of these ingredients, and levels of incorporation thereof, will depend on the physical form of the composition and the nature of the operation for which it is to be used. However, when one or more ingredients are present, such one or more ingredients may be present as detailed below.

Surfactants. Surfactants may be of the anionic, nonionic, zwitterionic, ampholytic or cationic type or may comprise compatible mixtures of these types. Anionic and nonionic surfactants are typically employed if the product is a laundry detergent. In contrast, cationic surfactants are typically employed if the product is a fabric softener. In addition to the anionic surfactant, the product may further contain a non-ionic surfactant. The product may contain up to from 0.01% to 30%, alternatively from 0.01% to 20%, more alternatively from 0.1% to 10%, by weight of the product, of a nonionic surfactant. In some examples, the nonionic surfactant may include an ethoxylated nonionic surfactant. Suitable for use herein are the ethoxylated alcohols and ethoxylated alkyl phenols of the formula $R(OC_2H_4)_n OH$, wherein R is selected from the group consisting of aliphatic hydrocarbon radicals containing from 8 to 20 carbon atoms and alkyl phenyl radicals in which the alkyl groups contain from 8 to 12 carbon atoms, and the average value of n is from 5 to 15.

Suitable nonionic surfactants are those of the formula $R^1(OC_2H_4)_nOH$, wherein $R^1$ is a $C_{10}$-$C_{16}$alkyl group or a $C_8$-$C_{12}$alkyl phenyl group, and n is from 3 to 80. In one aspect, particularly useful materials are condensation products of $C_9$-$C_{15}$ alcohols with from 5 to 20 moles of ethylene oxide per mole of alcohol.

Fabric and home care compositions may contain up to 30%, alternatively from 0.01% to 20%, more alternatively from 0.1% to 20%, by weight of the product, of a cationic surfactant. Cationic surfactants include those which can deliver fabric care benefits, non-limiting examples which include: fatty amines; quaternary ammonium surfactants; and imidazoline quat materials.

Builders. The product may also contain 0.1% to 80% by weight of the product of a builder. Compositions in liquid form generally contain 1% to 10% by weight of the product of the builder component. Compositions in granular form generally contain 1% to 50% by weight of the product of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions composed of a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of $SiO_2$ to alkali metal oxide of from 0.5 to 4, or from 1 to 2.4. Also useful are aluminosilicates including zeolites.

Dispersants. The product may contain from 0.1% to 10%, by weight of the product of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes. The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the product are from 0.0001% to 5% by weight of the product. When enzymes are present, they can be used at very low levels, e.g., from 0.001% or lower;

or they can be used in heavier-duty laundry detergent formulations at higher levels, e.g., 0.1% and higher. In accordance with a preference of some consumers for "non-biological" detergents, the products may be either or both enzyme-containing and enzyme-free.

Dye Transfer Inhibiting Agents. The product may also include from 0.0001%, from 0.01%, from 0.05% by weight of the product to 10%, 2%, or even 1% by weight of the product of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant. The product may contain less than 5%, or from 0.01% to 3%, by weight of the product, of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners. The product may also include a brightener (also referred to as "optical brightener") and may include any compound that exhibits fluorescence, including compounds that absorb UV light and reemit as "blue" visible light. Non-limiting examples of useful brighteners include derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those sold under the trademark Tinopal-UNPA-GX® by Ciba Specialty Chemicals Corporation (High Point, NC).

Bleach System. Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer. The product may contain one or more stabilizers and thickeners. Any suitable level of stabilizer may be of use; exemplary levels include from 0.01% to 20%, from 0.1% to 10%, or from 0.1% to 3% by weight of the product. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g., xanthan gum), polyvinyl alcohol and derivatives thereof, cellulose and derivatives thereof including cellulose ethers and cellulose esters and tamarind gum (for example, including xyloglucan polymers), guar gum, locust bean gum (in some aspects comprising galactomannan polymers), and other industrial gums and polymers.

Deposition Aid. In some examples, the fabric and home care product may include from 0.01% to 10%, from 0.05% to 5%, or from 0.15% to 3%, by weight of the product, of a deposition aid. In some examples, the deposition aid may be a cationic or amphoteric polymer. In some examples, the cationic polymer may have a cationic charge density of from 0.005 to 23 meq/g, from 0.01 to 12 meq/g, or from 0.1 to 7 meq/g, at the pH of the composition. For amine-containing polymers, wherein the charge density depends on the pH of the composition, charge density is measured at the intended use pH of the product. Such pH will generally range from 2 to 11, more generally from 2.5 to 9.5. Charge density is calculated by dividing the number of net charges per repeating unit by the molecular weight of the repeating unit. The positive charges may be located on the backbone of the polymers and/or the side chains of polymers.

In some examples, the deposition aid may include a cationic acrylic based polymer. In a further aspect, the deposition aid may include a cationic polyacrylamide. In another aspect, the deposition aid may include a polymer composed of polyacrylamide and polymethacrylamidopropyl trimethylammonium cation. In another aspect, the deposition aid may be composed of poly(acrylamide-N-dimethyl aminoethyl acrylate) and its quaternized derivatives.

In some examples, the deposition aid may be selected from the group of cationic or amphoteric polysaccharides. In some examples, the deposition aid may be selected from the group of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from 500 Daltons to 5,000,000 Daltons, e.g., 1,000 Daltons to 2,000,000 Daltons and 2,500 Daltons to 1,500,000 Daltons, as determined by size exclusion chromatography relative to polyethylene oxide standards with RI detection. In some examples, the MW of the cationic polymer may be 500 Daltons to 37,500 Daltons.

Silicones. Suitable silicones include Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may include a viscosity of from 10 to 2,000,000 centistokes at 25° C. In another aspect, suitable organosilicones may have a viscosity of from 10 to 800,000 centistokes at 25° C.

Suitable organosilicones may be linear, branched or cross-linked. In some examples, the organosilicone may be a cyclic silicone. The cyclic silicone may be a cyclomethicone of the formula $[(CH_3)_2SiO]_n$ where n is an integer that may range from 3 to 7, or from 5 to 6.

In some examples, the organosilicone may include a functionalized siloxane polymer. Functionalized siloxane polymers may include one or more functional moieties selected from the group of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In some examples, the functionalized siloxane polymer may include a silicone polyether, also referred to as "dimethicone copolyol." In general, silicone polyethers include a polydimethylsiloxane backbone with one or more polyoxyalkylene chains. The polyoxyalkylene moieties may be incorporated in the polymer as pendent chains or as terminal blocks. In some examples, the functionalized siloxane polymer may include an aminosilicone.

In some examples, the organosilicone may include amine ABn silicones and quat ABn silicones. Such organosilicones are generally produced by reacting a diamine with an epoxide.

Fabric Softening Actives. Non-limiting examples of fabric softening actives are N,N-bis(stearoyl-oxy-ethyl) N,N-dimethyl ammonium chloride, N,N-bis(tallowoyl-oxyethyl) N,N-dimethyl ammonium chloride, N,N-bis(stearoyl-oxy-ethyl)N-(2 hydroxyethyl)N-methyl ammonium methylsulfate; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above. It will be understood that combinations of softener actives disclosed above are suitable for use herein.

Fabric Hueing Agents. The product may further include a fabric hueing agent (sometimes referred to as shading, bluing or whitening agents). Typically, the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Color Index (CI) classifications of Acid, Direct, Basic, Reactive or hydrolyzed Reactive, Solvent or Disperse dyes for example that are classified as Blue, Violet, Red, Green or Black, and provide the desired shade either alone or in combination.

Suitable polymeric dyes include polymeric dyes selected from the group of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

Suitable dye clay conjugates include dye clay conjugates selected from the group comprising at least one cationic/basic dye and a smectite clay, and mixtures thereof.

The hueing agent may be incorporated into the product as part of a reaction mixture which is the result of the organic synthesis for a dye molecule, with optional purification step(s). Such reaction mixtures generally include the dye molecule itself and in addition may include un-reacted starting materials and/or by-products of the organic synthesis route.

Pigments. Suitable pigments include pigments selected from the group of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

Structurants. Useful structurants that may be added to adequately suspend a benefit agent or microcapsule include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, CA; Degussa AG or Dusseldorf, Germany; BASF AG of Ludwigshafen, Germany; Rhodia Corp. of Cranbury, NJ; Baker Hughes Corp. of Houston, TX; Hercules Corp. of Wilmington, DE; Agrium Inc. of Calgary, Alberta, Canada; ISP of NJ.

Anti Agglomeration Agents. Useful anti-agglomeration agents include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For Example, a value disclosed as "50%" is intended to mean "about 50%."

The terms "include," "includes," and "including," are meant to be non-limiting.

The terms "capsule" and "microcapsule" herein are used interchangeably.

The term "curing" as used in polymer chemistry and process engineering refers to a toughening or hardening process of a polymer by cross-linking of polymer chains, brought about by heat, chemical additives, or light radiation.

As used herein, a "core-shell microcapsule," or more generically a "microcapsule" or "capsule," is a substantially spherical structure having a well-defined core and a well-defined envelope or wall. Ideally, the wall protects the core against deterioration by oxygen, moisture, light, and effect of other compounds or other factors; limits the losses of volatile core materials; and releases the core material under desired conditions. In this respect, the core-shell microcapsules of this invention provide controlled release of the active material. As used herein, "controlled release" refers to retention of the active material in the core until a specified triggering condition occurs. Such triggers include, e.g., friction, swelling, a pH change, an enzyme, a change in temperature, a change in ionic strength, or a combination thereof.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

Microcapsule Composition 1 was prepared following the procedure described below.

An oil phase was first prepared by mixing 126 grams (g) of a model fragrance and 15 g of caprylic/capric triglyceride (a core solvent, commercially available under the trade name of NEOBEE® oil M-5, Stepan, Chicago, IL), and an aliphatic polyisocyanate (4.3 g) (a polyisocyanate based on hexamethylene diisocyanate (HDI) commercially available under Desmodur® N100A, Covestro, Leverkusen, Germany). In a separate beaker, 283.7 g of a pectin aqueous solution was obtained by dissolving pectin and 1,4-diazabicyclo[2.2.2]octane (DABCO, Evonik, Allentown, PA). The pectin aqueous solution was mixed with a solution (86 g) of 2.5% polystyrene sulfonate (commercially available under the trademark of FLEXAN® II from Akzo Nobel, Bridgewater, NJ) and 0.75% CMC (carboxymethyl cellulose, WALOCEL® CRT 50000 PA 07, Dow, Midland, MI) to form an aqueous phase. The oil phase was then emulsified into the aqueous phase to form an oil-in-water emulsion under a shearing rate of 7500 revolutions per minute ("RPM") for two minutes. A solution of 20% ammonium persulfate (APS, a catalyst) was then added to the emulsion. The oil-in-water emulsion was warmed to 25° C., to which 65 g of 10% tannic acid aqueous solution (Sigma-Aldrich, St. Louis, MO) was added under constant mixing. The resultant capsule slurry was cured at 55° C. for 1 hour. A 30% lysine aqueous solution (20 g, Sigma-Aldrich, St. Louis, MO) was then introduced to the capsule slurry. The mixture was stirred at 75° C. for 2 hours to obtain Microcapsule composition 1.

The formulation of Microcapsule composition 1 is shown in Table 1 below.

TABLE 1

|  | Weight amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Pectin | 5.2 | 0.8 |
| tannic acid | 6.5 | 1.1 |
| DABCO | 0.2 | 0.03 |
| Lysine (optional) | 6 | 1 |
| APS | 0.78 | 0.13 |
| Add water to | 600 | 100 |

Examples 2-20

Following the procedure described in Example 1, Microcapsules Compositions 2-20 of this invention are prepared using the agents and their amounts listed in Tables 2-20 below.

TABLE 2

Microcapsule Composition 2 with 0.4% pectin

|  | Weight amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Pectin | 2.4 | 0.4 |
| tannic acid | 6.5 | 1.1 |
| DABCO | 0.2 | 0.03 |
| APS | 0.78 | 0.13 |
| Add water to | 600 | 100 |

TABLE 3

Microcapsule Composition 3 with xanthan gum

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |

TABLE 3-continued

Microcapsule Composition 3 with xanthan gum

|  | Amount (g) | Composition (%) |
| --- | --- | --- |
| Xanthan gum | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 4

Microcapsule Composition 4 with cornstarch

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Cornstarch | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 5

Microcapsule Composition 5 with gum arabic

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Gum Arabic | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 6

Microcapsule Composition 6 with locust bean gum

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Locust Bean Gum | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 7

Microcapsule Composition 7 with maltodextrin

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Maltodextrin | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 8

Microcapsule Composition 8 with potato starch

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| Potato Starch | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 9

Microcapsule Composition 9 with sodium alginate

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| sodium alginate | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 10

Microcapsule Composition 10 with xyloglucan

|  | Amount (g) | Composition (%) |
| --- | --- | --- |
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| xyloglucan | 5.2 | 0.8 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 11

Microcapsule Composition 11 with 1.1% pectin

|  | Amount (g) | Composition (%) |
|---|---|---|
| fragrance | 126 | 22.7 |
| Caprylic/capric triglyceride | 15 | 2.5 |
| Polyisocyanate | 4.3 | 0.7 |
| Polystyrene sulfonate | 2.1 | 0.3 |
| carboxymethyl cellulose | 0.6 | 0.1 |
| pectin | 6.6 | 1.1 |
| tannic acid | 6.5 | 1.1 |
| DABCO | 0.2 | 0.03 |
| APS | 0.78 | 0.13 |
| lysine | 6 | 1 |
| Add water to | 600 | 100 |

TABLE 12

Microcapsule Composition 12 with 0.14% polyisocyanate

|  | Amount (g) | Composition (%) |
|---|---|---|
| fragrance | 126 | 22.7 |
| Caprylic/capric triglyceride | 15 | 2.5 |
| Polyisocyanate | 0.84 | 0.14 |
| Polystyrene sulfonate | 2.1 | 0.3 |
| carboxymethyl cellulose | 0.6 | 0.1 |
| Pectin | 4.8 | 0.8 |
| tannic acid | 9.8 | 1.6 |
| DABCO | 0.2 | 0.03 |
| APS | 0.78 | 0.13 |
| lysine | 6 | 1 |
| Add water to | 600 | 100 |

TABLE 13

Microcapsule Composition 13 with 0.27% polyisocyanate

|  | Amount (g) | Composition (%) |
|---|---|---|
| fragrance | 126 | 22.7 |
| Caprylic/capric triglyceride | 15 | 2.5 |
| Polyisocyanate | 1.62 | 0.27 |
| Polystyrene sulfonate | 2.1 | 0.3 |
| carboxymethyl cellulose | 0.6 | 0.1 |
| pectin | 4.8 | 0.8 |
| tannic acid | 9.8 | 1.6 |
| DABCO | 0.2 | 0.03 |
| APS | 0.78 | 0.13 |
| lysine | 6 | 1 |
| Add water to | 600 | 100 |

TABLE 14

Microcapsule Composition 14 with 0.48% polyisocyanate

|  | Amount (g) | Composition (%) |
|---|---|---|
| fragrance | 126 | 22.7 |
| Caprylic/capric triglyceride | 15 | 2.5 |
| Polyisocyanate | 2.9 | 0.48 |
| Polystyrene sulfonate | 2.1 | 0.3 |
| carboxymethyl cellulose | 0.6 | 0.1 |
| pectin | 4.8 | 0.8 |
| tannic acid | 9.8 | 1.6 |
| DABCO | 0.2 | 0.03 |
| APS | 0.78 | 0.13 |
| lysine | 6 | 1 |
| Add water to | 600 | 100 |

TABLE 15

Microcapsule Composition 15 with 1.6% tannic acid

|  | Amount (g) | Composition (%) |
|---|---|---|
| fragrance | 150 | 25 |
| Caprylic/capric triglyceride | 15 | 2.5 |
| Polyisocyanate | 4.2 | 0.7 |
| Polystyrene sulfonate | 2.1 | 0.3 |
| carboxymethyl cellulose | 0.6 | 0.1 |
| pectin | 4.8 | 0.8 |
| tannic acid | 9.8 | 1.6 |
| DABCO | 0.2 | 0.03 |
| APS | 0.78 | 0.13 |
| lysine | 6 | 1 |
| Add water to | 600 | 100 |

TABLE 16

Microcapsule Composition 16 with 2% tannic acid

|  | Amount (g) | Composition (%) |
|---|---|---|
| fragrance | 126 | 22.7 |
| Caprylic/capric triglyceride | 15 | 2.5 |
| Polyisocyanate | 5.4 | 0.9 |
| Polystyrene sulfonate | 2.1 | 0.3 |
| carboxymethyl cellulose | 0.6 | 0.1 |
| pectin | 4.8 | 0.8 |
| tannic acid | 12 | 2 |
| DABCO | 0.2 | 0.03 |
| APS | 0.78 | 0.13 |
| lysine | 6 | 1 |
| Add water to | 600 | 100 |

TABLE 17

Microcapsule Composition 17 with 2.9% tannic acid

|  | Amount (g) | Composition (%) |
|---|---|---|
| fragrance | 168 | 28 |
| Caprylic/capric triglyceride | 18 | 3 |
| Polyisocyanate | 6 | 1 |
| Polystyrene sulfonate | 2.1 | 0.3 |
| carboxymethyl cellulose | 0.6 | 0.1 |
| pectin | 5.4 | 0.9 |
| tannic acid | 17.5 | 2.9 |
| DABCO | 0.2 | 0.03 |
| APS | 0.78 | 0.13 |
| lysine | 6 | 1 |
| Add water to | 600 | 100 |

TABLE 18

Microcapsule Composition 18 with 3.1% tannic acid

|  | Amount (g) | Composition (%) |
|---|---|---|
| fragrance | 192 | 32 |
| Caprylic/capric triglyceride | 18 | 3 |
| Polyisocyanate | 6.6 | 1.1 |
| Polystyrene sulfonate | 2.1 | 0.3 |
| carboxymethyl cellulose | 0.6 | 0.1 |
| pectin | 4.8 | 0.8 |
| tannic acid | 18.6 | 3.1 |
| DABCO | 0.2 | 0.03 |
| APS | 0.78 | 0.13 |
| lysine | 6 | 1 |
| Add water to | 600 | 100 |

TABLE 19

Microcapsule Composition 19 without tannic acid

|  | Amount (g) | Composition (%) |
|---|---|---|
| fragrance | 126 | 22.7 |
| Caprylic/capric triglyceride | 15 | 2.5 |
| Polyisocyanate | 4.2 | 0.7 |
| Polystyrene sulfonate | 2.1 | 0.3 |
| carboxymethyl cellulose | 0.6 | 0.1 |
| pectin | 4.8 | 0.8 |
| DABCO | 0.2 | 0.03 |
| APS | 0.78 | 0.13 |
| lysine | 6 | 1 |
| Add water to | 600 | 100 |

TABLE 20

Microcapsule Composition 20 without tannic acid

|  | Amount (g) | Composition (%) |
|---|---|---|
| fragrance | 126 | 22.7 |
| Caprylic/capric triglyceride | 15 | 2.5 |
| Polyisocyanate | 4.2 | 0.7 |
| Polystyrene sulfonate | 2.1 | 0.3 |
| carboxymethyl cellulose | 0.6 | 0.1 |
| pectin | 4.8 | 0.8 |
| DABCO | 0.2 | 0.03 |
| Add water to | 600 | 100 |

Examples 21-22 Formulation without Dispersants

Microcapsule Compositions 21 and 22 of this invention did not contain a dispersant. They were prepared using a xylene diisocyanate based polyisocyanate (commercially available as Takenate™ D-110N from Mitsui Corporation, New York, NY). Briefly, one hundred and twenty-six grams of a fragrance accord (International Flavors and Fragrance, Union Beach, NJ) was weighed out and combined with 15 g of caprylic/capric triglyceride (NEOBEE® oil M-5, Stepan, Chicago, IL) and 4.3 g of an aromatic polyisocyanate (trimethylol propane-adduct of xylylene diisocyanate, Takenate™ D-110N) to form the oil phase. In a separate beaker, a solution (369.7 g) containing 1.5% of pectin and 0.06% DABCO Crystalline (Evonik, Allentown, PA) was prepared to form the aqueous phase. The oil phase was then emulsified into the aqueous phase to form the fragrance emulsion under shearing at 7500 rpm for two minutes. The fragrance emulsion was heated to 25° C. in a round bottom vessel under constant mixing with an overhead mixer. The mixer speed was reduced after addition was completed. 85 grams of water was added under stirring. The capsule slurry was cured at 55° C. for one hour. A 30% lysine aqueous solution (20 g) was then introduced to crosslink with any unreacted isocyanate groups on the polyisocyanate. The slurry was further cured at 75° C. for two hours.

The formulations of Microcapsule Compositions 21 and 22 of this invention are shown in Tables 21-22 below.

TABLE 21

Microcapsule Composition 21

|  | Amount (g) | Composition (%) |
|---|---|---|
| fragrance | 126 | 22.7 |
| Caprylic/capric triglyceride | 15 | 2.5 |
| Polyisocyanate | 4.3 | 0.7 |
| Pectin | 5.8 | 1 |
| Triethylenediamine | 0.2 | 0.03 |
| Add water to | 600 | 100 |

TABLE 22

Microcapsule Composition 22

|  | Amount (g) | Composition (%) |
|---|---|---|
| fragrance | 126 | 22.7 |
| Caprylic/capric triglyceride | 15 | 2.5 |
| Polyisocyanate | 4.3 | 0.7 |
| Pectin | 5.8 | 1 |
| Triethylenediamine | 0.2 | 0.03 |
| Lysine | 6 | 1 |
| Add water to | 600 | 100 |

Preparation of Comparative Capsule Composition

Comparative Composition MF was prepared as follows. A reactor was charged with 34 g of an acrylic acid-acrylamide copolymer solution, 18 g of a melamine-formaldehyde pre-condensate, and 293 g of water. This mixture was stirred until a clear solution with an approximate pH of 6.3 is obtained. Acetic acid was added until pH 5 was reached. This mixture was then stirred for 1 hour at 23° C. at which time 210 g of the fragrance core consisting of 168 g of a model fragrance and 42 g of Neobee® M-5 oil was added and the mixture high-sheared until a mean droplet size of 8 µm was reached. The temperature was raised to 80° C. for 2 hours to cure the microcapsules. After 2 hours 40 g of water was added and the mixture was cooled. Upon cooling a white slurry with pH 5-6 was obtained. 25 g of ethylene urea were added. A white slurry was obtained. The pH of the slurry was adjusted to pH 7 by sodium hydroxide solution.

Example 23: Microcapsule Composition Prepared from OSA-Modified Starch

Microcapsule Composition 23 was prepared as follows. An oil phase was obtained by mixing 34.33 g of a model fragrance and 8.58 g of caprylic/capric triglyceride (NEOBEE® oil M-5), and an aliphatic polyisocyanate (0.7 g, Desmodur® N100A). In a separate beaker, an aqueous phase was prepared by mixing an aqueous dispersion (46 g) containing 10% of an OSA-modified starch (commercially available under the tradename of Purity Gum® Ultra from Ingredion, Inc., Westchester, Illinois), an aqueous solution (5.8 g) of a 10% sodium salt of polystyrene sulfonate (Flexan® II), an aqueous solution (1.2 g) of 20% DABCO crystalline, and water (12.83 g). The oil phase was then emulsified into the aqueous phase to form an oil-in-water emulsion under shearing at 9600 rpm for three minutes.

After the oil-in-water emulsion was stirred at 25° C. for 0.5 hours, 3.81 g of 30% tannic acid aqueous solution (Tanal®-01, Ajinomoto, Japan) was added. The resultant mixture was cured at 25° C. for 1 hour and then at 80° C. for 4 hours to obtain Microcapsule Composition 23. Table 23 below shows the components added to make the microcapsule composition. The encapsulation efficiency is 99.9%.

Examples 23A were prepared in the same way except that an aromatic polyisocyanate (trimethylol propane-adduct of xylylene diisocyanate) was used instead of the aliphatic polyisocyanate.

TABLE 23

|  | Amount (g) | Composition (%) |
|---|---|---|
| fragrance | 34.33 | 30 |
| Caprylic/capric triglyceride | 8.58 | 7.6 |
| Polyisocyanate | 0.7 | 0.6 |
| OSA-modified Starch | 4.6 | 4.1 |
| sodium salt of polystyrene sulfonate | 0.58 | 0.5 |
| DABCO | 0.24 | 0.02 |
| Tannic acid | 1.14 | 1 |
| Total weight | 113 | 100 |

Example 24: OSA-Starch Microcapsule

Microcapsule Composition 24 was prepared following the procedure described in Example 23 using the components shown in Table 24 below. The encapsulation efficiency is 99.9%.

TABLE 24

|  | Amount (g) | Composition (%) |
|---|---|---|
| fragrance | 40 | 35 |
| Caprylic/capric triglyceride | 10 | 8.8 |
| Polyisocyanate[1] | 0.7 | 0.6 |
| OSA-modified Starch[2] | 2.86 | 2.5 |
| Modified waxy maize starch[3] | 1.14 | 1 |
| sodium salt of polystyrene sulfonate | 0.58 | 0.5 |
| DABCO | 0.24 | 0.02 |
| Tannic acid | 1.14 | 1 |
| Total weight | 114 | 100 |

[1]Desmodur ® N100A.
[2]Purity Gum ® Ultra.
[3]Capsul ® 6330 from Ingredion.

Example 25

Microcapsule Composition 25 was prepared following the procedure described in Example 23 using the components shown in Table 25 below. The encapsulation efficiency is 99.9%.

TABLE 25

|  | Amount (g) | Composition (%) |
|---|---|---|
| fragrance | 45.8 | 35 |
| Caprylic/capric triglyceride | 11 | 8.8 |
| Polyisocyanate[1] | 0.7 | 0.6 |
| OSA-modified Starch[2] | 2.86 | 2.5 |
| Modified waxy maize starch[3] | 1.14 | 1 |
| sodium salt of polystyrene sulfonate | 0.58 | 0.5 |
| CMC | 0.29 | 0.25 |
| DABCO | 0.24 | 0.02 |
| Tannic acid | 1.14 | 1 |
| Total weight | 114 | 100 |

[1]Desmodur ® N100A.
[2]Purity Gum ® Ultra.
[3]Capsul ® 6330.

Example 26

Microcapsule Composition 26 was prepared as follows. An oil phase was first obtained by mixing 45.8 g of a model fragrance and 11.14 g of caprylic/capric triglyceride (NEOBEE® oil M-5), and an aliphatic polyisocyanate (0.458 g, Desmodur® N100A). In a separate beaker, an aqueous phase was prepared by mixing an aqueous dispersion (28.61 g) containing 10% OSA-modified starch (Purity Gum® Ultra), an aqueous solution (11.44 g) of 10% modified waxy maize starch (Capsul® 6330), an aqueous solution (5.8 g) of a 10% sodium salt of polystyrene sulfonate (Flexan® II), an aqueous solution (5.8 g) of 1% CMC, an aqueous solution (0.12 g) of 20% DABCO crystalline, and water (0.626 g). The oil phase was then emulsified into the aqueous phase to form an oil-in-water emulsion under shearing at 9600 rpm for three minutes.

After the oil-in-water emulsion was stirred at 25° C. for 0.5 hours, 3.81 g of 30% tannic acid aqueous solution (Tanal®-01), and 0.86 g of 40% glyoxal aqueous solution (Sigma-Aldrich, US) were added under constant mixing. The mixture was cured at 25° C. for 1 hour and then at 80° C. for 4 hours. Table 26 below shows the components used to prepare the microcapsule composition. The encapsulation efficiency is 99.9%.

TABLE 26

|  | Amount (g) | Composition (%) |
|---|---|---|
| fragrance | 45.8 | 40 |
| Caprylic/capric triglyceride | 11 | 10 |
| Polyisocyanate[1] | 0.458 | 0.4 |
| OSA-modified Starch[2] | 2.86 | 2.5 |
| Modified waxy maize starch[3] | 1.14 | 1 |
| glyoxal | 0.344 | 0.3 |
| sodium salt of polystyrene sulfonate | 0.58 | 0.5 |
| CMC | 0.058 | 0.05 |
| DABCO | 0.24 | 0.02 |
| Tannic acid | 1.14 | 1 |
| Total weight | 114 | 100 |

[1]Desmodur ® N100A.
[2]Purity Gum ® Ultra or High-Cap ® 100.
[3]Capsul ® 6330.

Examples 27A, 27B, and 27C

Microcapsule Composition 27A was prepared by adding a rheology modifier to Microcapsule Composition 1 at an amount of 1% by weight of the microcapsule composition. The Rheology modifier was an anionic hydrophobically modified alkali-soluble acrylic polymer emulsion (HASE) (commercially available under Aculyn® 22 from Dow Chemical, Midland, Michigan).

Microcapsule Compositions 27B and 27C were prepared by adding xanthan gum at 0.15% and 0.3%, respectively. Stability evaluation showed that Examples 27A-C were more stable (with much less water separation) as compared to Microcapsule Composition 1. All samples were stored at 25° C. and 37° C. for at least 8 weeks.

Fragrance Performance Studies in an EU Fabric Conditioner Base

To establish the performance of the microcapsule compositions of this invention, Microcapsule Composition 1 was blended into a model fabric conditioner base to obtain Sample 1. The fragrance load was 0.6% neat oil equivalent (NOE). A representative base contains a quat surfactant (active) 1-20%, a stabilizer <1%, a pH buffer <1%, a salt <1%, a preservative <0.1%, and an antifoam <0.1, all by weight of the base.

The perfumery benefit of the capsules was evaluated by conducting a laundry experiment using accepted experimental protocols using European wash machine. Terry towels were used for the washing experiments and were washed with the fabric conditioner Sample 1. The fragrance intensity is evaluated after post rubbing of the towels by gas chromatography-mass spectrometry (GC/MS). The pre-rubbing intensity refers to the GC/MS reading of the fragrance released before rubbing the towel. The post-rubbing intensity refers the GC/MS reading after rubbing the towel three times. The results are in Table 27.

TABLE 27

| Samples | Pre-rubbing intensity | Post-rubbing intensity |
|---|---|---|
| Example 1 | 18308 | 94836 |
| MF | 21675 | 48424 |
| Neat fragrance | 2770 | 3986 |

Microcapsule Composition 25 was also evaluated. It was formulated into the model fabric conditioner base to obtain Sample 2 at 0.6% NOE. Terry towels were treated as described above and then evaluated by a panel of 12 trained judges. The fragrance intensity was rated by a scale ranging from 0 to 35. A numerical value of 4 would suggest the fabric only produce weak intensity while a value of 30 indicates the subject generate a very strong smell. The pre-gentle tossing intensity refers to fragrance intensity score after folding the towels twice. The results are shown in Table 28 below. Comparative Composition MF and the fragrance neat oil were evaluated side-by-side with Sample 2.

TABLE 28

| Sample | Pre-toss intensity | Gentle-toss intensity | Post-rub intensity |
|---|---|---|---|
| Sample 2 | 7.9 | 9.3 | 12.7 |
| MF | 7.7 | 8.2 | 11.3 |
| Neat oil | 0 | 1 | 1 |

Consumer Product Examples

Microcapsule compositions of this invention can be added to various consumer products. Non-limiting examples are shown in Table 29 below.

TABLE 29

| Fabric Softener | Antiperspirant (AP) roll-on product |
|---|---|
| Microcapsule Composition, 0.1-2% NOE[2]<br>Quat surfactant (active), 1-20%<br>Stabilizer, <1%<br>pH buffer, <1%<br>Salt, <1%<br>Preservative, <0.1%<br>Antifoam, <0.1<br>Water, q.s. to 100% | Microcapsule Composition, 0.1-2% NOE<br>Anionic surfactant, 1-3%<br>Aluminum chlorohydrate, 10-20%,<br>Silica, less than 1%<br>Helianthus annuus, 1-2%<br>Water, q.s. to 100% |
| Shampoo | Hair conditioner |
| Microcapsule Composition, 0.1-2% NOE<br>Sodium lauryl ether sulphate, 12%<br>Cocamidopropyl betaine, 1.6%<br>Non-ionic guar, 0.2%<br>Silicone, 2-3%<br>Preservative, 0.5%<br>Water, q.s. to 100% | Microcapsule Composition, 0.1-2% NOE<br>Fatty alcohol, 4%<br>Behentrimonium chloride, 0.7%<br>Terminal amino silicones, 1%<br>Silicone, 2.5%<br>Preservative, 0.5%<br>Water, q.s. to 100% |
| Powder detergent Example 1 | Powder detergent Example 2 |
| Microcapsule Composition, 0.1-2% NOE<br>Sodium Carbonate, 81.9%<br>Ethoxylated $C_{12}$-$C_{15}$ alcohol sulfate salt, 4.3%<br>$C_{12}$-$C_{15}$ alcohol ethoxylate, 2.4%<br>Sodium Sulfate, 1.5%<br>Sodium bicarbonate, 1.3%<br>Sodium polyacrylate, 0.7%<br>Sodium Carboxymethylcellulose, 0.1%<br>Optical Brightener, 0.2%<br>Polyvinyl Alcohol, 0.1%<br>Water, 7.4% | Microcapsule Composition, 0.1-2% NOE<br>Sodium alkl benzene sulphonate, 7.6%<br>Nonionic surfactant, 9.8%<br>Soap, 1.7%<br>sodium aluminosilicate (zeolite), 27%<br>Sodium Carbonate, 13%<br>Alkaline sodium silicate (1:3.3), 0.5%<br>CP5-polymer ex BASF, 4%<br>Sodium Carboxymethylcellulose (SCMC), 0.6%<br>Water, 11%<br>Minors, 1.5%<br>Dry Additives<br>Sodium perborate monohydrate (PBM), 14%<br>Enzyme, 1.1%<br>TAED granules (83%), 7.4%<br>Ethylene diamine tetramethylene phosphonate (EDTMP), 0.4%<br>anti-foam granules, 0.4% |
| Powder detergent Example 3 | Roll on deodorant |
| Microcapsule Composition, 0.1-2% NOE<br>Zeolite, 36.6-45.9%<br>Sodium carbonate, 13.3-16.6% | Microcapsule Composition, 0.1-2% NOE<br>Aluminum Chlorohydrate 50% Solution, 30-34%<br>Steareth-20, 1.3-1.9% |

TABLE 29-continued

| | |
|---|---|
| Soap, 0-0.7% | Steareth-2, 5-5.6% |
| Sodium sulphate, 0-2% | Silica, 0.5-1.1% |
| Sodium Carboxymethylcellulose (SCMC), 0-0.9% | Preservative, 0.7-1.3% |
| Fluorescer, 0-0.7% | |
| Sodium alkyl benzene sulphonate, 0-23.3% | |
| Primary Alkyl sulphate, 0-23.1% | |
| Nonionic 7 EO surfactant, 0-4.1% | |
| Nonionic 3 EO surfactant, 0-7% | |
| CP5 co-polymer ex BASF, 1-3% | |
| Alkaline Sodium silicate, 0-4% | |
| Water, 11.5-15.8% | |

Liquid detergent

Microcapsule Composition, 0.1-2% NOE
A non-soap surfactant (anionic or nonionic) with a range of 15 wt. % to 45 wt. %, preferably 32 wt. % to 35 wt. %
Propylene glycol, 0.5-50%, preferably 10-20%
One or more soil release polymer (SRP) that can be between 0.01% and 10%, preferably 0.9% and 2.5%,
Water, 5-35%, preferably 15-25%

[1]All component percentages are shown by weight of the consumer product.
[2]NOE is the neat fragrance oil equivalence which equals to the weight percentage of the fragrance oil in the consumer product.

OTHER EMBODIMENTS

All of the features disclosed in this specification may be combined in any combination. Each feature disclosed in this specification may be replaced by an alternative feature serving the same, equivalent, or similar purpose.

To achieve the purpose of encapsulating an active material, one skilled in the art can design and prepare a capsule composition by using different encapsulating polymers, coatings, and capsule formation aids, varying the concentrations of wall-forming materials or catalysts to achieve desirable release profiles in a consumable product. Further, the ratios among the wall forming materials, capsule forming aids, adjuvents, core modifiers, active materials, and catalysts can also be determined by a skilled artisan through known assays.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising microcapsules that contain a microcapsule core and a microcapsule wall encapsulating the microcapsule core, wherein
the microcapsule core contains an active material, and
the microcapsule wall is a covalently bonded polymeric network comprising
  (i) a pectin;
  (ii) a polyisocyanate; and
  (iii) a tannic acid;
wherein the pectin and the polyisocyanate are covalently bonded, and the polyisocyanate and the tannic acid are also covalently bonded.

2. The microcapsule composition of claim 1, wherein the tannic acid is present at a level of 0.1% to 5% by weight of the microcapsule composition.

3. A method of preparing the microcapsule composition of claim 1, comprising the steps of:
  (a) preparing an oil-in-water emulsion comprising the active material, the pectin, and the polyisocyanate;
  (b) adding the tannic acid to the oil-in-water emulsion; and
  (c) applying conditions sufficient to induce formation of a covalently bonded polymeric network comprising the pectin, polyisocyanate and tannic acid, thereby forming the microcapsule composition,
wherein the pectin and the polyisocyanate are covalently bonded, and the polyisocyanate and the tannic acid are also covalently bonded.

4. The microcapsule composition of claim 1 further comprising a capsule formation aid.

5. The microcapsule composition of claim 1, wherein the active material contains a fragrance, flavor, cosmetic active, malodor counteractant, or a combination thereof.

6. The microcapsule composition of claim 1, wherein the polyisocyanate is selected from the group consisting of a polyisocyanurate of toluene diisocyanate, a trimethylol propane-adduct of toluene diisocyanate, a trimethylol propane-adduct of xylylene diisocyanate, a biuret of hexamethylene diisocyanate, and combinations thereof.

7. The microcapsule composition of claim 1, wherein the microcapsules are present at a level of 10% to 50% by weight of the mierocapsule composition.

8. The microcapsule composition of claim 1, wherein the pectin has a molecular weight of 200 Da to 2,000,000 Da.

9. The microcapsule composition of claim 1, wherein the pectin has a molecular weight of 10,000 Da to 500,000 Da.

10. The microcapsule composition of claim 1, wherein the pectin has molecular weight of 30,000 Da to 200,000 Da.

11. A consumer product comprising the microcapsule composition of claim 1.

* * * * *